(12) United States Patent
Lee

(10) Patent No.: US 6,191,261 B1
(45) Date of Patent: Feb. 20, 2001

(54) GROWTH DIFFERENTIATION FACTOR-9 ANTIBODIES AND METHODS

(75) Inventor: Se-Jin Lee, Baltimore, MD (US)

(73) Assignee: The Johns Hopkins University School of Medicine, Baltimore, MD (US)

( * ) Notice: Under 35 U.S.C. 154(b), the term of this patent shall be extended for 0 days.

(21) Appl. No.: 09/172,062

(22) Filed: Oct. 13, 1998

Related U.S. Application Data

(60) Division of application No. 08/491,835, filed on Oct. 23, 1995, now Pat. No. 5,821,056, which is a continuation-in-part of application No. 08/003,303, filed on Jan. 12, 1993, now abandoned.

(30) Foreign Application Priority Data

Jan. 12, 1994 (WO) .................................. PCT/US94/00685

(51) Int. Cl.$^7$ .................................................... C07K 16/00
(52) U.S. Cl. .............................. 530/388.24; 530/388.23; 530/387.1; 530/387.9; 530/389.2; 530/391.3; 530/388.1; 435/7.1
(58) Field of Search .............................. 530/387.1, 387.9, 530/388.23, 388.24, 389.2, 391.3, 388.1; 435/7.1; 436/512

(56) References Cited

U.S. PATENT DOCUMENTS 5,821,056   10/1998   Lee .

FOREIGN PATENT DOCUMENTS

WO 92/00382   1/1992   (WO) .

OTHER PUBLICATIONS

Dong et al., "Growth differentiation factor–9 is required during early ovarian folliculogenesis," *Nature* 383:531–535 (1996).

Fitzpatrick et al., "Expression of Growth Differentiation Factor–9 Messenger Ribonucleic Acid in Ovarian and Nonovarian Rodent and Human Tissues," *Endocrinology* 139(5):2571–2578 (1998).

Se–Jin Lee, "Expression of growth/differentiation factor 1 in the nervous system: Conservation of a bicistronic structure," *Proc. Natl. Acad. Sci. USA*, 88:4250–4254 (May 1991).

Se–Jin Lee, "Identification of a Novel Member (GDF–1) of the Transforming Growth Factor–β Superfamily," *Molecular Endocrinology*, 0888–8809/90/1034–1040 (1990).

McPherron and Lee, "GDF–3 and GDF–9: Two New Members of the Transforming Growth Factor–β Superfamily Containing a Novel Pattern of Cysteines," *The Journal of Biological Chemistry*, 268(5):3444–3449 (Feb. 1993).

Bowie et al. Science 247:1307–1310, 1990.

Rudinger. Peptide Homones, Parsons, ed., University Park Press, Baltimore, pp 1–7, 1976.

Wells, Biochemistry 29:85–7–17, 1990.

Ngo et al. The Protein Folding Problem and Tertiary Structure Prediction. Merz et al., eds., Birkhauser, Boston, pp. 491–495, 1994.

Massague. Cell 49:437–438, 1987.

Callard et al. The Cytokine FactsBook, Academic Press, London, pp. 31–32, 1994.

*Primary Examiner*—Elizabeth Kemmerer
(74) *Attorney, Agent, or Firm*—Gray, Cary, Ware & Freidenrich LLP; Lisa A. Haile

(57) ABSTRACT

Growth differentiation factor-9 (GDF-9) is disclosed along with its polynucleotide sequence and amino acid sequence. Also disclosed are diagnostic and therapeutic methods of using the GDF-9 polypeptide and polynucleotide sequences.

9 Claims, 15 Drawing Sheets

```
  1  ATGGCGTTCCTCTTAGTTCTTCCAAGTCATGGCACTTCCTGTGGGGT    60
        M  A  L  P  S  N  F  L  L  G  V
 61  TTGCTGCTTGCCTGGTCTGTTTTCTTAGTAGCCTTAGCTTCTGAAGA   120
      C  C  F  A  W  L  C  F  L  S  S  L  S  Q  A  S  T  E  E
121  ATCCCAGAGTGGAGAGCCAGTGAAATGTGGAGTCTGAGGCAGACCCCTGGTCCTTGCTGCT   180
      S  Q  S  G  A  S  E  N  V  E  S  E  A  D  P  W  S  L  L  L
181  GCCCTGTAGAATGGGACACAGTTCGGCCTCCCCCTCTTGCCCCCTCTTAAGGTTCTATCTGA   240
      P  V  D  G  T  D  R  S  G  L  L  P  P  L  F  K  V  L  S  D
241  TAGGCGAGGTGAGACCCCTAAGCTACCAAAGAGGGGTTCCCAGCAGGTTCACTACATGAAAA   300
      R  R  G  E  T  P  K  L  Q  P  D  S  R  A  L  Y  Y  M  K  K
301  GCTCTATAAGACGTATGCTAGTCCCTGTGCCCAGCAAGAGCAGGCACCCAGCAACCAGT   360
      L  Y  K  T  Y  A  T  K  E  G  V  P  K  P  S  R  S  H  L  Y
361  CAATACCGTCCGGCTCTTCAGTCCCTGTGCCCAGCAGGAGCAGGCACCCAGCAACCAGT   420
      N  T  V  R  L  F  S  P  C  A  Q  Q  E  Q  A  P  S  N  Q  V
421  GACAGGACCGCCTGCCGATGGTGGACCTGCTGTTTAACCTGGACCGGGTGACTGCCATGGA   480
      T  G  P  L  P  M  V  D  L  L  F  N  L  D  R  V  T  A  M  E
481  ACACTTGCTCAAATCGGTCTTGCTATACACTCTGAACAACTCGCCTCCTCCTCCAC   540
      H  L  K  S  V  L  L  Y  T  L  N  S  A  S  S  S  T
541  TGTGACCTGTATGTGACTTGTGTGTAAAGGAGGCCATGTCTTCTGCAGGCACCCCC   600
      V  T  C  M  C  D  L  V  V  K  E  A  M  S  S  G  R  A  P  P
```

FIG. 2A

```
 601  AAGAGCACCGTACTCATTCACCCTGAAGAAACAGATGGATTGAGATGTGACCTC   660
      R  S  T  V  L  I  H  L  K  K  H  R  W  I  E  I  D  V  T  S
 661  CCTCCTTCAGCCCCTAGTGACCTGAGTGAGGAGCATTCACCTGTCAATTTTAC    720
      L  L  Q  P  L  V  T  S  S  E  R  S  I  H  L  S  V [N  F  T]
 721  ATGCACAAAAGACCAGGTGCCAGGAGACGGAGTGTTTAGCATGCCTCTCAGTGCCTCC 780
      C  T  K  D  Q  V  P  E  D  G  V  F  S  M  P  L  S  V  P  P
 781  TTCCCTCATCTTGTATCTCAACGACACAAGCCAGCCTACCACTCTTGGCAGTCTCT    840
      S [L  I  L  Y  L  N  D  T] S  T  Q  A  Y  H  S  W  Q  S  L
 841  TCAGTCCACCTGGAGGCCTTTACAGCATCCCCGGTGTGGCCGTGCCCCGT       900
      Q  S  T  W  R  P  L  Q  H  P  G  Q  A  G  V  A  A  R  P  V
 901  GAAAGAGGAAGCTACTGAGGTGGAAAGATCTCCCGGCCGTCGAGGCCAGAAAGCCAT   960
      K  E  E  A  T  E  V  E  R  S  P [R  R  R] G  Q  K  A  I
 961  CCGGTCCGAAGCGGGCCCTCTTACTCCTTCAACTCCGAATACTTCAA        1020
      R  S  E  A  K  G  P  L  L  T  A  S  F [N  L  S] E  Y  F  K
1021  ACAGTTTCTTTTCCCCAAAACTGTGAACTCCATGACTGTCAGAGTTTAGTCA      1080
      Q  F  L  F  P  Q  N  E  C  E  L  H  D  F  R  L  S  F  S  Q
1081  GCTCAAATGGACAACTGGATCGTGGCCCCACAGGTACAACCCTAGTACTGTAAAGG   1140
      L  K  W  D  N  W  I  V  A  P  H  R  Y  N  P  R  Y  C  K  G
```

FIG. 2B

```
1141  GGACTGTCCTAGGGCGGTCAGGCATCGGTATGGCTCCTGTGCACACCATGGTCCAGAA   1200
       D   C   P   R   A   V   R   H   R   Y   G   S   P   V   H   T   M   V   Q   N
1201  TATAATCTATGAGAAGCTGGACCCCTTCAGTGTCCCAAGGCCTTCGTGTGCCGGGCAAGTA   1260
       I   I   Y   E   K   L   D   P   S   V   P   R   P   S   C   V   P   G   K   Y
1261  CAGCCCCCGAGTGTGTTGACCATTGAACCTGACGGCTCCATCGCTTACAAAGAGTACGA   1320
       S   P   L   S   V   L   T   I   E   P   D   G   S   I   A   Y   K   E   Y   E
1321  AGACATGATAGCTACGAGGTGCACCTGTCGTTAGCAGGCCACTTCAACAAGCCTGC   1380
       D   M   I   A   T   R   C   T   C   R   *
1381  CTGGCAGAGCAATGCTGTGGGCCTTAGAGTGCCTGGCAGAGAGCTTCCTGACCAGTC   1440
1441  TCTCCGTGCTGCTCAGTGTCCGTGCTCAGCGTGTGAGCGGGAAGTGTGTGTGATGAGCA   1500
1501  CATCGAGTGCTCAGTGTCCGTAGTGTAAAGGGCACACTCACTGTCGTTGCCATAAACCAA   1560
1561  GTGAAATGTAACTCATTGGAGAGCTCTTTCTCCCACGAGTGTAGTTTTCAGTGGACAG   1620
1621  ATTTGTTAGCATAAGTCTCGAGTAGAATGTCTGTGAACATGTCAGAGTCAGACAG   1680
1681  TATGTGACGGAAGAATAAACTGTTGATGGCAT  1712
```

FIG. 2C

```
GDF-3       KRRAAISVPKGFC--RNFHRHQLFINF-QDLGWHKWVIAPKGFMANYCQGQCPFSMTTYLNS--
GDF-9       FNLSEYFKQFLFP--QNEELHDFRLSF-SQLKWDNWIVAPHRYNPRYCKGDCPRAVRHRYGS--

GDF-1       PRRDAEPVLGGGP--GGARARRLYVSF-REVGWHRWVIAPRGFLANYCQGQCALPVALSGSGGP
Vg-1        RRKRSYSKLPFTA--SNICKKRHLYVEF-KDVGWQNWVIAPQGYMANYCYGECPYPLTEILNG--
Vgr-1       RVSSASDYNSSEL--KTARKHELYVSF-QDLGWQDWIIAPKGYAANYCDGECSFPLNAHMNA--
OP-1        RMANVAENSSSDQ--RQACKKHELYVSF-RDLGWQDWIIAPEGYAAYYCEGECAFPLNSYMNA--
BMP-5       RMSSVGDYNTSEQ--KQACKKHELYVSF-RDLGWQDWIIAPEGYAAFYCDGECSFPLNAHMNA--
60A         SPNNVPLLEPMES--TRSCQMQTLYIDF-KDLGWHDWIIAPEGYGAFYCSGECNFPLNAHMNA--
BMP-2       EKRQAKHKQRKRL--KSSCKRHPLYVDF-KDLGWHDWIIAPPGYHAFYCHGECPFPLADHLNS--
BMP-4       RSPKHHSQRARKK--NKNCRRHSLYVDF-SDVGWNDWIVAPPGYQAFYCHGDCPFPLADHLNS--
DPP         KRHARRPTRKNH--DDTCRRHSLYVDF-SDVGWDDWIVAPLGYDAYYCHGKCPFPLADHFNS--
BMP-3       QTLKKARRKQWIE--PRNCARRYLKVDF-ADIGWSEWIISPKSFDAYYCSGACQFPMPKSLKP--
MIS         PGRAQRSAGATAA--DGPCALRELSVDL----RAERSVLIPETYQANNCQGVCGWPQSDRNPRY-
Inhibin α    LRLLQRPPEEPAA--HANCHRVALNISF-QELGWERWIVYPPSFIFHYCHGGCGLHIPPNLSLPV
Inhibin βA   RRRRGLECDGKV---NICKKQFFVSF-KDIGWNDWIIAPSGYHANYCEGECPSHIAGTSGSSL
Inhibin βB   RIRKRGLECDGRT---NLCCRQQFFIDF-RLIGWNDWIIAPTGYYGNYCEGSCPAYLAGVPGSAS
TGF-β1      RRALDTNYCFSST---EKNCCVRQLYIDFRKDLGWKWIHEPKGYHANFCLGPCPYIWSLD----
TGF-β2      KRALDAAYCFRNV--QDNCCLRPLYIDFRKDLGWKWIHEPKGYNANFCAGACPYLWSSD----
TGF-β3      KRALDTNYCFRNL--EENCCVRPLYIDFRQDLGWKWVHEPKGYYANFCSGPCPYLRSAD----
TGF-β4      RRDLDTDYCFGPGTDEKNCCVRPLYIDFRQDLGWKWIHEPKGYYANFCMGPCPYIWSAD----
TGF-β5      KRGVGQEYCFGNN--GPNCCVKPLYINFRKDLGWKWIHEPKGYEANYCLGNCPYIWSMD----
```

| | GDF-3 | GDF-9 | GDF-1 | Vg-1 | Vgr-1 | OP-1 | BMP-5 | 60A | BMP-2 | BMP-4 | DPP |
|---|---|---|---|---|---|---|---|---|---|---|---|
| TGF-β5 | 36 | 25 | 32 | 34 | 37 | 36 | 36 | 36 | 35 | 33 | 35 |
| TGF-β4 | 33 | 22 | 34 | 32 | 39 | 37 | 36 | 38 | 33 | 32 | 33 |
| TGF-β3 | 32 | 25 | 33 | 37 | 39 | 38 | 36 | 40 | 36 | 35 | 35 |
| TGF-β2 | 31 | 25 | 32 | 36 | 37 | 38 | 35 | 39 | 34 | 33 | 35 |
| TGF-β1 | 36 | 23 | 33 | 34 | 35 | 34 | 34 | 38 | 35 | 34 | 35 |
| INHIBIN βB | 41 | 31 | 35 | 37 | 41 | 42 | 37 | 39 | 42 | 42 | 42 |
| INHIBIN βA | 42 | 30 | 37 | 44 | 44 | 43 | 43 | 36 | 42 | 41 | 39 |
| INHIBIN α | 25 | 27 | 23 | 22 | 25 | 24 | 24 | 24 | 22 | 22 | 19 |
| MIS | 22 | 21 | 34 | 30 | 24 | 27 | 24 | 25 | 27 | 27 | 25 |
| BMP-3 | 42 | 29 | 42 | 49 | 44 | 42 | 43 | 41 | 48 | 47 | 43 |
| DPP | 47 | 32 | 41 | 48 | 59 | 58 | 57 | 54 | 74 | 75 | 100 |
| BMP-4 | 50 | 34 | 43 | 56 | 60 | 58 | 59 | 54 | 92 | 100 | - |
| BMP-2 | 53 | 33 | 42 | 58 | 61 | 60 | 61 | 57 | 100 | - | - |
| 60A | 47 | 30 | 41 | 51 | 71 | 69 | 74 | 100 | - | - | - |
| BMP-5 | 50 | 31 | 46 | 56 | 91 | 88 | 100 | - | - | - | - |
| OP-1 | 50 | 30 | 47 | 57 | 87 | 100 | - | - | - | - | - |
| Vgr-1 | 53 | 31 | 46 | 58 | 100 | - | - | - | - | - | - |
| Vg-1 | 57 | 30 | 57 | 100 | - | - | - | - | - | - | - |
| GDF-1 | 50 | 27 | 100 | - | - | - | - | - | - | - | - |
| GDF-9 | 33 | 100 | - | - | - | - | - | - | - | - | - |
| GDF-3 | 100 | - | - | - | - | - | - | - | - | - | - |

FIG. 4A

|  | BMP-3 | MIS | INHIBIN α | INHIBIN βA | INHIBIN βB | TGF-β1 | TGF-β2 | TGF-β3 | TGF-β4 | TGF-β5 |
|---|---|---|---|---|---|---|---|---|---|---|
| TGF-β5 | 30 | 26 | 24 | 36 | 28 | 82 | 70 | 73 | 79 | 100 |
| TGF-β4 | 27 | 29 | 24 | 33 | 30 | 86 | 68 | 74 | 100 | - |
| TGF-β3 | 32 | 25 | 24 | 36 | 37 | 78 | 82 | 100 | - | - |
| TGF-β2 | 32 | 23 | 22 | 37 | 34 | 74 | 100 | - | - | - |
| TGF-β1 | 32 | 28 | 23 | 41 | 35 | 100 | - | - | - | - |
| INHIBIN βB | 37 | 25 | 25 | 63 | 100 | - | - | - | - | - |
| INHIBIN βA | 36 | 24 | 26 | 100 | - | - | - | - | - | - |
| INHIBIN α | 29 | 18 | 100 | - | - | - | - | - | - | - |
| MIS | 30 | 100 | - | - | - | - | - | - | - | - |
| BMP-3 | 100 | - | - | - | - | - | - | - | - | - |
| DPP | - | - | - | - | - | - | - | - | - | - |
| BMP-4 | - | - | - | - | - | - | - | - | - | - |
| BMP-2 | - | - | - | - | - | - | - | - | - | - |
| 60A | - | - | - | - | - | - | - | - | - | - |
| BMP-5 | - | - | - | - | - | - | - | - | - | - |
| OP-1 | - | - | - | - | - | - | - | - | - | - |
| Vgr-1 | - | - | - | - | - | - | - | - | - | - |
| Vg-1 | - | - | - | - | - | - | - | - | - | - |
| GDF-1 | - | - | - | - | - | - | - | - | - | - |
| GDF-9 | - | - | - | - | - | - | - | - | - | - |
| GDF-3 | - | - | - | - | - | - | - | - | - | - |

FIG. 4B

```
  1 MALPSNFLLGVCCFAWLCFLSSLSSQASTEESQSGASENVESEADPWSLL  50
    || |   |||  ||||||||  ||  ||||  | |  ||   || | |||||
  1 MARPNKFLLWFCCFAWLCFPISLGSQASGGEAQIAASAELESGAMPWSLL  50

51 LPVDGTDRSGLLPPLFKVLSDRRGETPKLQPDSRALYYMKKLYKTYATKE 100
        |  |||| ||||||  ||  |  | ||||||||  |||||||||||||
 51 QHIDERDRAGLLPALFKVLSVGRGGSPRLQPDSRALHYMKKLYKTYATKE 100

101 GVPKPSRSHLYNTVRLFSPCAQQEQAPSNQVTGPLPMVDLLFNLDRVTAM 150
    | || |||||||||||| ||    |||  |||| || ||  |||||| |
101 GIPKSNRSHLYNTVRLFTPCTRHKQAPGDQVTGILPSVELLFNLDRITTV 150

151 EHLLKSVLLYTLNNSASSSSTVTCMCDLVVKEAMSSGRAPPRAPYSFTL. 199
    |||||||||  |||  || |  |  |  | ||   ||  |  |||||||
151 EHLLKSVLLYNINNSVSFSSAVKCVCNLMIKEPKSSRTLGRAPYSFTFN  200

200 ......KKHRWIEIDVTSLLQPLVTSSERSIHLSVNFTCTKDQV....PE 239
          ||| || |||||||||||| |    ||||  | ||||  |||
201 SQFEFGKKHKWIQIDVTSLLQPLVASNKRSIHMSINFTCMKDQLEHPSAQ 250

240 DGVFSMPLSVPPSLILYLNDTSTQAYHSWQSLQSTWRPLQHPGQA.GVAA 288
    | | | |  ||||||||||||  |||||| ||   || ||     |   |
251 NGLFNMTL.VSPSLILYLNDTSAQAYHSWYSLHYKRRPSQGPDQERSLSA 299

289 RPVKEEATEVERSP..RRRRGQKAIRSEAKGPLLTASFNLSEYFKQFLFP 336
    || |||  | ||   |||||   ||  |  || | ||||||||||| |
300 YPVGEEAAEDGRSSHHRHRRGQETVSSELKKPLGPASFNLSEYFRQFLLP 349

337 QNEEELHDFRLSFSQLKWDNWIVAPHRYNPRYCKGDCPRAVRHRYGSPVH 386
    ||||||||||||||||||||||||||||||||||||||||| |||||||
350 QNEEELHDFRLSFSQLKWDNWIVAPHRYNPRYCKGDCPRAVGHRYGSPVH 399

387 TMVQNIIYEKLDPSVPRPSCVPGKYSPLSVLTIEPDGSIAYKEYEDMIAT 436
    |||||||||||| |||||| ||  ||||||||||||||||||||||||
400 TMVQNIIYEKLDSSVPRPSCVPAKYSPLSVLTIEPDGSIAYKEYEDMIAT 449

437 RCTCR 441
    | | |
450 KCTCR 454
```

FIG. 7a
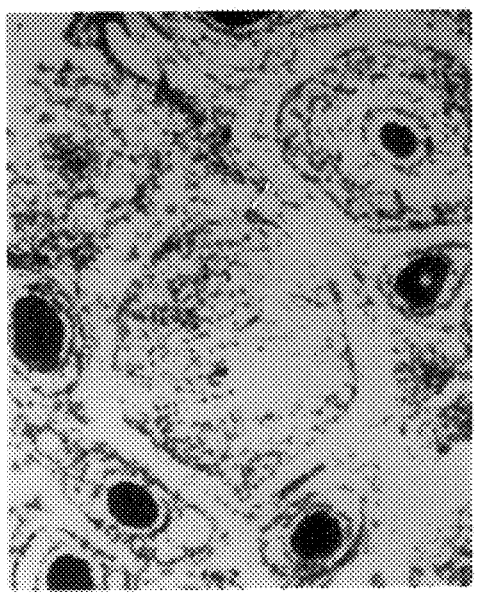
FIG. 7b
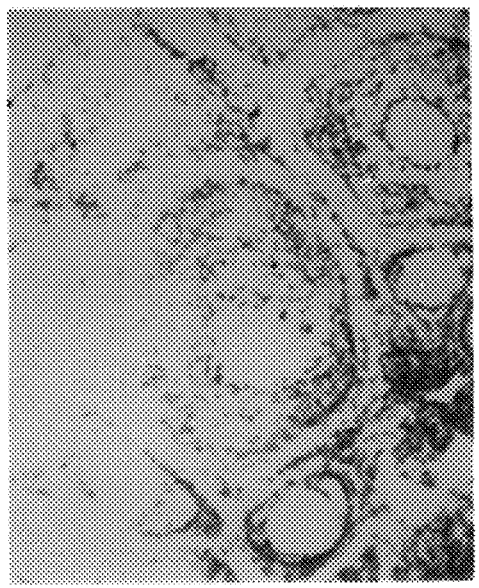
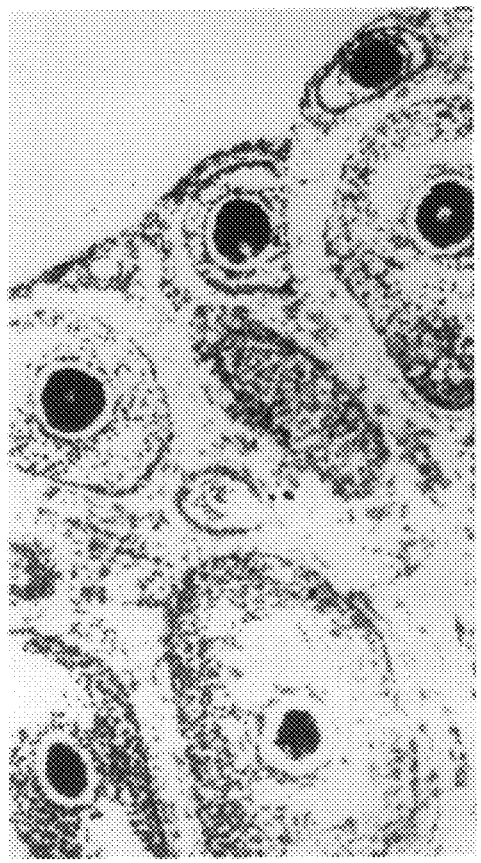
FIG. 7c
FIG. 7d

```
                           SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
         (A) LENGTH: 35 base pairs
         (B) TYPE: nucleic acid
         (C) STRANDEDNESS: single
         (D) TOPOLOGY: linear (ii) MOLECULE TYPE: DNA (genomic)

(vii) IMMEDIATE SOURCE:
         (B) CLONE: SJL160

(ix) FEATURE:
         (A) NAME/KEY: CDS
         (B) LOCATION: 1..35
         (D) OTHER INFORMATION: /note= "Where "B" occurs, B =
             inosine"

(xi) SEQUENCE DESCRIPTION: SEQ ID NO:1:

CCGGAATTCG GBTGGVANVA NTGGRTBRTB KCBCC                              35

(2) INFORMATION FOR SEQ ID NO:2:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (ii) MOLECULE TYPE: DNA (genomic)

(vii) IMMEDIATE SOURCE:
         (B) CLONE: SJL153

(ix) FEATURE:
         (A) NAME/KEY: CDS
         (B) LOCATION: 1..33
```

(xi) SEQUENCE DESCRIPTION: SEQ ID NO:2:

CCGGAATTCR CADSCRCADC YNBTDGYDRY CAT                              33

(2) INFORMATION FOR SEQ ID NO:3:

(i) SEQUENCE CHARACTERISTICS:
        (A) LENGTH: 1712 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: GDF-9

(ix) FEATURE:
        (A) NAME/KEY: CDS
        (B) LOCATION: 29..1351

(xi) SEQUENCE DESCRIPTION: SEQ ID NO:3:

```
ATGCGTTCCT TCTTAGTTCT TCCAAGTC ATG GCA CTT CCC AGC AAC TTC CTG         52
                              Met Ala Leu Pro Ser Asn Phe Leu
                                1               5

TTG GGG GTT TGC TGC TTT GCC TGG CTG TGT TTT CTT AGT AGC CTT AGC       100
Leu Gly Val Cys Cys Phe Ala Trp Leu Cys Phe Leu Ser Ser Leu Ser
     10              15                  20

TCT CAG GCT TCT ACT GAA GAA TCC CAG AGT GGA GCC AGT GAA AAT GTG      148
Ser Gln Ala Ser Thr Glu Glu Ser Gln Ser Gly Ala Ser Glu Asn Val
 25              30                  35                  40

GAG TCT GAG GCA GAC CCC TGG TCC TTG CTG CTG CCT GTA GAT GGG ACT      196
Glu Ser Glu Ala Asp Pro Trp Ser Leu Leu Leu Pro Val Asp Gly Thr
                 45                  50                  55

GAC AGG TCT GGC CTC TTG CCC CCC CTC TTT AAG GTT CTA TCT GAT AGG      244
Asp Arg Ser Gly Leu Leu Pro Pro Leu Phe Lys Val Leu Ser Asp Arg
             60                  65                  70

CGA GGT GAG ACC CCT AAG CTG CAG CCT GAC TCC AGA GCA CTC TAC TAC      292
Arg Gly Glu Thr Pro Lys Leu Gln Pro Asp Ser Arg Ala Leu Tyr Tyr
         75                  80                  85

ATG AAA AAG CTC TAT AAG ACG TAT GCT ACC AAA GAG GGG GTT CCC AAA      340
Met Lys Lys Leu Tyr Lys Thr Tyr Ala Thr Lys Glu Gly Val Pro Lys
     90                  95                 100

CCC AGC AGA AGT CAC CTC TAC AAT ACC GTC CGG CTC TTC AGT CCC TGT      388
Pro Ser Arg Ser His Leu Tyr Asn Thr Val Arg Leu Phe Ser Pro Cys
105                 110                 115                 120

GCC CAG CAA GAG CAG GCA CCC AGC AAC CAG GTG ACA GGA CCG CTG CCG      436
Ala Gln Gln Glu Gln Ala Pro Ser Asn Gln Val Thr Gly Pro Leu Pro
                125                 130                 135

ATG GTG GAC CTG CTG TTT AAC CTG GAC CGG GTG ACT GCC ATG GAA CAC      484
Met Val Asp Leu Leu Phe Asn Leu Asp Arg Val Thr Ala Met Glu His
            140                 145                 150

TTG CTC AAA TCG GTC TTG CTA TAC ACT CTG AAC AAC TCT GCC TCT TCC      532
Leu Leu Lys Ser Val Leu Leu Tyr Thr Leu Asn Asn Ser Ala Ser Ser
        155                 160                 165

TCC TCC ACT GTG ACC TGT ATG TGT GAC CTT GTG GTA AAG GAG GCC ATG      580
Ser Ser Thr Val Thr Cys Met Cys Asp Leu Val Val Lys Glu Ala Met
170                 175                 180

TCT TCT GGC AGG GCA CCC CCA AGA GCA CCG TAC TCA TTC ACC CTG AAG      628
Ser Ser Gly Arg Ala Pro Pro Arg Ala Pro Tyr Ser Phe Thr Leu Lys
185                 190                 195                 200

AAA CAC AGA TGG ATT GAG ATT GAT GTG ACC TCC CTC CTT CAG CCC CTA      676
Lys His Arg Trp Ile Glu Ile Asp Val Thr Ser Leu Leu Gln Pro Leu
```

```
                 205                 210                 215
GTG ACC TCC AGC GAG AGG AGC ATT CAC CTG TCT GTC AAT TTT ACA TGC      724
Val Thr Ser Ser Glu Arg Ser Ile His Leu Ser Val Asn Phe Thr Cys
            220                 225                 230

ACA AAA GAC CAG GTG CCA GAG GAC GGA GTG TTT AGC ATG CCT CTC TCA      772
Thr Lys Asp Gln Val Pro Glu Asp Gly Val Phe Ser Met Pro Leu Ser
            235                 240                 245

GTG CCT CCT TCC CTC ATC TTG TAT CTC AAC GAC ACA AGC ACC CAG GCC      820
Val Pro Pro Ser Leu Ile Leu Tyr Leu Asn Asp Thr Ser Thr Gln Ala
            250                 255                 260

TAC CAC TCT TGG CAG TCT CTT CAG TCC ACC TGG AGG CCT TTA CAG CAT      868
Tyr His Ser Trp Gln Ser Leu Gln Ser Thr Trp Arg Pro Leu Gln His
265                 270                 275                 280

CCC GGC CAG GCC GGT GTG GCT GCC CGT CCC GTG AAA GAG GAA GCT ACT      916
Pro Gly Gln Ala Gly Val Ala Ala Arg Pro Val Lys Glu Glu Ala Thr
                285                 290                 295

GAG GTG GAA AGA TCT CCC CGG CGC CGT CGA GGG CAG AAA GCC ATC CGC      964
Glu Val Glu Arg Ser Pro Arg Arg Arg Arg Gly Gln Lys Ala Ile Arg
            300                 305                 310

TCC GAA GCG AAG GGG CCA CTT CTT ACA GCA TCC TTC AAC CTC AGC GAA     1012
Ser Glu Ala Lys Gly Pro Leu Leu Thr Ala Ser Phe Asn Leu Ser Glu
            315                 320                 325

TAC TTC AAA CAG TTT CTT TTC CCC CAA AAC GAG TGT GAA CTC CAT GAC     1060
Tyr Phe Lys Gln Phe Leu Phe Pro Gln Asn Glu Cys Glu Leu His Asp
            330                 335                 340

TTC AGA CTG AGT TTT AGT CAG CTC AAA TGG GAC AAC TGG ATC GTG GCC     1108
Phe Arg Leu Ser Phe Ser Gln Leu Lys Trp Asp Asn Trp Ile Val Ala
345                 350                 355                 360

CCG CAC AGG TAC AAC CCT AGG TAC TGT AAA GGG GAC TGT CCT AGG GCG     1156
Pro His Arg Tyr Asn Pro Arg Tyr Cys Lys Gly Asp Cys Pro Arg Ala
                365                 370                 375

GTC AGG CAT CGG TAT GGC TCT CCT GTG CAC ACC ATG GTC CAG AAT ATA     1204
Val Arg His Arg Tyr Gly Ser Pro Val His Thr Met Val Gln Asn Ile
            380                 385                 390

ATC TAT GAG AAG CTG GAC CCT TCA GTG CCA AGG CCT TCG TGT GTG CCG     1252
Ile Tyr Glu Lys Leu Asp Pro Ser Val Pro Arg Pro Ser Cys Val Pro
            395                 400                 405

GGC AAG TAC AGC CCC CTG AGT GTG TTG ACC ATT GAA CCC GAC GGC TCC     1300
Gly Lys Tyr Ser Pro Leu Ser Val Leu Thr Ile Glu Pro Asp Gly Ser
            410                 415                 420

ATC GCT TAC AAA GAG TAC GAA GAC ATG ATA GCT ACG AGG TGC ACC TGT     1348
Ile Ala Tyr Lys Glu Tyr Glu Asp Met Ile Ala Thr Arg Cys Thr Cys
425                 430                 435                 440

CGT TAGCATGGGG GCCACTTCAA AAGCCTGCCC TGGCAGAGCA ATGCTGTGGG          1401
Arg

CCTTAGAGTG CCTGGGCAGA GAGCTTCCTG TGACCAGTCT CTCCGTGCTG CTCAGTGCAC    1461

ACTGTGTGAG CGGGGGAAGT GTGTGTGTGT GGATGAGCAC ATCGAGTGCA GTGTCCGTAG    1521

GTGTAAAGGG CACACTCACT GGTCGTTGCC ATAAACCAAG TGAAATGTAA CTCATTTGGA    1581

GAGCTCTTTC TCCCCACGAG TGTAGTTTTC AGTGGACAGA TTTGTTAGCA TAAGTCTCGA    1641

GTAGAATGTA GCTGTGAACA TGTCAGAGTG CTGTGGTTTT ATGTGACGGA AGAATAAACT    1701

GTTGATGGCA T                                                        1712
```

(2) INFORMATION FOR SEQ ID NO:4:

(i) SEQUENCE CHARACTERISTICS:
        (A) LENGTH: 441 amino acids
        (B) TYPE: amino acid -continued (D) TOPOLOGY: linear (ii) MOLECULE TYPE: protein (xi) SEQUENCE DESCRIPTION: SEQ ID NO:4:

```
Met Ala Leu Pro Ser Asn Phe Leu Leu Gly Val Cys Cys Phe Ala Trp
 1               5                  10                  15

Leu Cys Phe Leu Ser Ser Leu Ser Ser Gln Ala Ser Thr Glu Glu Ser
            20                  25                  30

Gln Ser Gly Ala Ser Glu Asn Val Glu Ser Glu Ala Asp Pro Trp Ser
        35                  40                  45

Leu Leu Leu Pro Val Asp Gly Thr Asp Arg Ser Gly Leu Leu Pro Pro
    50                  55                  60

Leu Phe Lys Val Leu Ser Asp Arg Arg Gly Glu Thr Pro Lys Leu Gln
65                  70                  75                  80

Pro Asp Ser Arg Ala Leu Tyr Tyr Met Lys Lys Leu Tyr Lys Thr Tyr
                85                  90                  95

Ala Thr Lys Glu Gly Val Pro Lys Pro Ser Arg Ser His Leu Tyr Asn
            100                 105                 110

Thr Val Arg Leu Phe Ser Pro Cys Ala Gln Gln Glu Gln Ala Pro Ser
        115                 120                 125

Asn Gln Val Thr Gly Pro Leu Pro Met Val Asp Leu Leu Phe Asn Leu
    130                 135                 140

Asp Arg Val Thr Ala Met Glu His Leu Leu Lys Ser Val Leu Leu Tyr
145                 150                 155                 160

Thr Leu Asn Asn Ser Ala Ser Ser Ser Thr Val Thr Cys Met Cys
                165                 170                 175

Asp Leu Val Val Lys Glu Ala Met Ser Ser Gly Arg Ala Pro Pro Arg
            180                 185                 190

Ala Pro Tyr Ser Phe Thr Leu Lys Lys His Arg Trp Ile Glu Ile Asp
        195                 200                 205

Val Thr Ser Leu Leu Gln Pro Leu Val Thr Ser Ser Glu Arg Ser Ile
    210                 215                 220

His Leu Ser Val Asn Phe Thr Cys Thr Lys Asp Gln Val Pro Glu Asp
225                 230                 235                 240

Gly Val Phe Ser Met Pro Leu Ser Val Pro Pro Ser Leu Ile Leu Tyr
                245                 250                 255

Leu Asn Asp Thr Ser Thr Gln Ala Tyr His Ser Trp Gln Ser Leu Gln
            260                 265                 270

Ser Thr Trp Arg Pro Leu Gln His Pro Gly Gln Ala Gly Val Ala Ala
        275                 280                 285

Arg Pro Val Lys Glu Glu Ala Thr Glu Val Glu Arg Ser Pro Arg Arg
    290                 295                 300

Arg Arg Gly Gln Lys Ala Ile Arg Ser Glu Ala Lys Gly Pro Leu Leu
305                 310                 315                 320

Thr Ala Ser Phe Asn Leu Ser Glu Tyr Phe Lys Gln Phe Leu Phe Pro
                325                 330                 335

Gln Asn Glu Cys Glu Leu His Asp Phe Arg Leu Ser Phe Ser Gln Leu
            340                 345                 350

Lys Trp Asp Asn Trp Ile Val Ala Pro His Arg Tyr Asn Pro Arg Tyr
        355                 360                 365

Cys Lys Gly Asp Cys Pro Arg Ala Val Arg His Arg Tyr Gly Ser Pro
    370                 375                 380

Val His Thr Met Val Gln Asn Ile Ile Tyr Glu Lys Leu Asp Pro Ser
```

```
                385                 390                 395                 400
Val Pro Arg Pro Ser Cys Val Pro Gly Lys Tyr Ser Pro Leu Ser Val
            405                 410                 415

Leu Thr Ile Glu Pro Asp Gly Ser Ile Ala Tyr Lys Glu Tyr Glu Asp
            420                 425                 430

Met Ile Ala Thr Arg Cys Thr Cys Arg
            435                 440

(2) INFORMATION FOR SEQ ID NO:5:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: GDF-3

(ix) FEATURE:
        (A) NAME/KEY: Protein
        (B) LOCATION: 1..117

(xi) SEQUENCE DESCRIPTION: SEQ ID NO:5:

Lys Arg Arg Ala Ala Ile Ser Val Pro Lys Gly Phe Cys Arg Asn Phe
1                   5                  10                  15

Cys His Arg His Gln Leu Phe Ile Asn Phe Gln Asp Leu Gly Trp His
                20                  25                  30

Lys Trp Val Ile Ala Pro Lys Gly Phe Met Ala Asn Tyr Cys His Gly
            35                  40                  45

Glu Cys Pro Phe Ser Met Thr Thr Tyr Leu Asn Ser Ser Asn Tyr Ala
        50                  55                  60

Phe Met Gln Ala Leu Met His Met Ala Asp Pro Lys Val Pro Lys Ala
65                  70                  75                  80

Val Cys Val Pro Thr Lys Leu Ser Pro Ile Ser Met Leu Tyr Gln Asp
                85                  90                  95

Ser Asp Lys Asn Val Ile Leu Arg His Tyr Glu Asp Met Val Val Asp
            100                 105                 110

Glu Cys Gly Cys Gly
        115

(2) INFORMATION FOR SEQ ID NO:6:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: GDF-9

(ix) FEATURE:
        (A) NAME/KEY: Protein
        (B) LOCATION: 1..118

(xi) SEQUENCE DESCRIPTION: SEQ ID NO:6:

Phe Asn Leu Ser Glu Tyr Phe Lys Gln Phe Leu Phe Pro Gln Asn Glu
1                   5                  10                  15

Cys Glu Leu His Asp Phe Arg Leu Ser Phe Ser Gln Leu Lys Trp Asp
```

```
                    20                  25                  30
Asn Trp Ile Val Ala Pro His Arg Tyr Asn Pro Arg Tyr Cys Lys Gly
            35                  40                  45
Asp Cys Pro Arg Ala Val Arg His Arg Tyr Gly Ser Pro Val His Thr
        50                  55                  60
Met Val Gln Asn Ile Ile Tyr Glu Lys Leu Asp Pro Ser Val Pro Arg
65                  70                  75                  80
Pro Ser Cys Val Pro Gly Lys Tyr Ser Pro Leu Ser Val Leu Thr Ile
                85                  90                  95
Glu Pro Asp Gly Ser Ile Ala Tyr Lys Glu Tyr Glu Asp Met Ile Ala
            100                 105                 110
Thr Arg Cys Thr Cys Arg
        115
```

(2) INFORMATION FOR SEQ ID NO:7:

(i) SEQUENCE CHARACTERISTICS:
        (A) LENGTH: 122 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: GDF-1

(ix) FEATURE:
        (A) NAME/KEY: Protein
        (B) LOCATION: 1..122

(xi) SEQUENCE DESCRIPTION: SEQ ID NO:7:

```
Pro Arg Arg Asp Ala Glu Pro Val Leu Gly Gly Gly Pro Gly Gly Ala
1               5                   10                  15
Cys Arg Ala Arg Arg Leu Tyr Val Ser Phe Arg Glu Val Gly Trp His
            20                  25                  30
Arg Trp Val Ile Ala Pro Arg Gly Phe Leu Ala Asn Tyr Cys Gln Gly
        35                  40                  45
Gln Cys Ala Leu Pro Val Ala Leu Ser Gly Ser Gly Gly Pro Pro Ala
50                  55                  60
Leu Asn His Ala Val Leu Arg Ala Leu Met His Ala Ala Ala Pro Gly
65                  70                  75                  80
Ala Ala Asp Leu Pro Cys Cys Val Pro Ala Arg Leu Ser Pro Ile Ser
                85                  90                  95
Val Leu Phe Phe Asp Asn Ser Asp Asn Val Val Leu Arg Gln Tyr Glu
            100                 105                 110
Asp Met Val Val Asp Glu Cys Gly Cys Arg
        115                 120
```

(2) INFORMATION FOR SEQ ID NO:8:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: Vg-1

(ix) FEATURE:

(A) NAME/KEY: Protein
        (B) LOCATION: 1..118

(xi) SEQUENCE DESCRIPTION: SEQ ID NO:8:

Arg Arg Lys Arg Ser Tyr Ser Lys Leu Pro Phe Thr Ala Ser Asn Ile
1               5                   10                  15

Cys Lys Lys Arg His Leu Tyr Val Glu Phe Lys Asp Val Gly Trp Gln
            20                  25                  30

Asn Trp Val Ile Ala Pro Gln Gly Tyr Met Ala Asn Tyr Cys Tyr Gly
        35                  40                  45

Glu Cys Pro Tyr Pro Leu Thr Glu Ile Leu Asn Gly Ser Asn His Ala
    50                  55                  60

Ile Leu Gln Thr Leu Val His Ser Ile Glu Pro Glu Asp Ile Pro Leu
65                  70                  75                  80

Pro Cys Cys Val Pro Thr Lys Met Ser Pro Ile Ser Met Leu Phe Tyr
            85                  90                  95

Asp Asn Asn Asp Asn Val Val Leu Arg His Tyr Glu Asn Met Ala Val
                100                 105                 110

Asp Glu Cys Gly Cys Arg
        115

(2) INFORMATION FOR SEQ ID NO:9:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: Vgr-1

(ix) FEATURE:
        (A) NAME/KEY: Protein
        (B) LOCATION: 1..118

(xi) SEQUENCE DESCRIPTION: SEQ ID NO:9:

Arg Val Ser Ser Ala Ser Asp Tyr Asn Ser Ser Glu Leu Lys Thr Ala
1               5                   10                  15

Cys Arg Lys His Glu Leu Tyr Val Ser Phe Gln Asp Leu Gly Trp Gln
            20                  25                  30

Asp Trp Ile Ile Ala Pro Lys Gly Tyr Ala Ala Asn Tyr Cys Asp Gly
        35                  40                  45

Glu Cys Ser Phe Pro Leu Asn Ala His Met Asn Ala Thr Asn His Ala
    50                  55                  60

Ile Val Gln Thr Leu Val His Leu Met Asn Pro Glu Tyr Val Pro Lys
65                  70                  75                  80

Pro Cys Cys Ala Pro Thr Lys Leu Asn Ala Ile Ser Val Leu Tyr Phe
            85                  90                  95

Asp Asp Asn Ser Asn Val Ile Leu Lys Lys Tyr Arg Asn Met Val Val
                100                 105                 110

Arg Ala Cys Gly Cys His
        115

(2) INFORMATION FOR SEQ ID NO:10:

(i) SEQUENCE CHARACTERISTICS:
        (A) LENGTH: 118 amino acids
        (B) TYPE: amino acid (C) STRANDEDNESS: single
          (D) TOPOLOGY: linear (ii) MOLECULE TYPE: protein (vii) IMMEDIATE SOURCE:
          (B) CLONE: OP-1

(ix) FEATURE:
          (A) NAME/KEY: Protein
          (B) LOCATION: 1..118

(xi) SEQUENCE DESCRIPTION: SEQ ID NO:10:

Arg Met Ala Asn Val Ala Glu Asn Ser Ser Asp Gln Arg Gln Ala
 1               5                  10                  15

Cys Lys Lys His Glu Leu Tyr Val Ser Phe Arg Asp Leu Gly Trp Gln
            20                  25                  30

Asp Trp Ile Ile Ala Pro Glu Gly Tyr Ala Ala Tyr Tyr Cys Glu Gly
                35                  40                  45

Glu Cys Ala Phe Pro Leu Asn Ser Tyr Met Asn Ala Thr Asn His Ala
         50                  55                  60

Ile Val Gln Thr Leu Val His Phe Ile Asn Pro Glu Thr Val Pro Lys
65                  70                  75                  80

Pro Cys Cys Ala Pro Thr Gln Leu Asn Ala Ile Ser Val Leu Tyr Phe
                85                  90                  95

Asp Asp Ser Ser Asn Val Ile Leu Lys Lys Tyr Arg Asn Met Val Val
                100                 105                 110

Arg Ala Cys Gly Cys His
        115

(2) INFORMATION FOR SEQ ID NO:11:

(i) SEQUENCE CHARACTERISTICS:
          (A) LENGTH: 118 amino acids
          (B) TYPE: amino acid
          (C) STRANDEDNESS: single
          (D) TOPOLOGY: linear (ii) MOLECULE TYPE: protein (vii) IMMEDIATE SOURCE:
          (B) CLONE: BMP-5

(ix) FEATURE:
          (A) NAME/KEY: Protein
          (B) LOCATION: 1..118

(xi) SEQUENCE DESCRIPTION: SEQ ID NO:11:

Arg Met Ser Ser Val Gly Asp Tyr Asn Thr Ser Glu Gln Lys Gln Ala
 1               5                  10                  15

Cys Lys Lys His Glu Leu Tyr Val Ser Phe Arg Asp Leu Gly Trp Gln
            20                  25                  30

Asp Trp Ile Ile Ala Pro Glu Gly Tyr Ala Ala Phe Tyr Cys Asp Gly
                35                  40                  45

Glu Cys Ser Phe Pro Leu Asn Ala His Met Asn Ala Thr Asn His Ala
         50                  55                  60

Ile Val Gln Thr Leu Val His Leu Met Phe Pro Asp His Val Pro Lys
65                  70                  75                  80

Pro Cys Cys Ala Pro Thr Lys Leu Asn Ala Ile Ser Val Leu Tyr Phe
                85                  90                  95

Asp Asp Ser Ser Asn Val Ile Leu Lys Lys Tyr Arg Asn Met Val Val
                100                 105                 110

Arg Ser Cys Gly Cys His
        115

(2) INFORMATION FOR SEQ ID NO:12:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: 60A (ix) FEATURE:
        (A) NAME/KEY: Protein
        (B) LOCATION: 1..118

(xi) SEQUENCE DESCRIPTION: SEQ ID NO:12:

Ser Pro Asn Asn Val Pro Leu Leu Glu Pro Met Glu Ser Thr Arg Ser
1               5                   10                  15

Cys Gln Met Gln Thr Leu Tyr Ile Asp Phe Lys Asp Leu Gly Trp His
            20                  25                  30

Asp Trp Ile Ile Ala Pro Glu Gly Tyr Gly Ala Phe Tyr Cys Ser Gly
        35                  40                  45

Glu Cys Asn Phe Pro Leu Asn Ala His Met Asn Ala Thr Asn His Ala
    50                  55                  60

Ile Val Gln Thr Leu Val His Leu Leu Glu Pro Lys Lys Val Pro Lys
65                  70                  75                  80

Pro Cys Cys Ala Pro Thr Arg Leu Gly Ala Leu Pro Val Leu Tyr His
            85                  90                  95

Leu Asn Asp Glu Asn Val Asn Leu Lys Lys Tyr Arg Asn Met Ile Val
            100                 105                 110

Lys Ser Cys Gly Cys His
        115

(2) INFORMATION FOR SEQ ID NO:13:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: BMP-2

(ix) FEATURE:
        (A) NAME/KEY: Protein
        (B) LOCATION: 1..117

(xi) SEQUENCE DESCRIPTION: SEQ ID NO:13:

Glu Lys Arg Gln Ala Lys His Lys Gln Arg Lys Arg Leu Lys Ser Ser
1               5                   10                  15

Cys Lys Arg His Pro Leu Tyr Val Asp Phe Ser Asp Val Gly Trp Asn
            20                  25                  30

Asp Trp Ile Val Ala Pro Pro Gly Tyr His Ala Phe Tyr Cys His Gly
        35                  40                  45

Glu Cys Pro Phe Pro Leu Ala Asp His Leu Asn Ser Thr Asn His Ala
    50                  55                  60

-continued

```
Ile Val Gln Thr Leu Val Asn Ser Val Asn Ser Lys Ile Pro Lys Ala
65                  70                  75                  80

Cys Cys Val Pro Thr Glu Leu Ser Ala Ile Ser Met Leu Tyr Leu Asp
                85                  90                  95

Glu Asn Glu Lys Val Val Leu Lys Asn Tyr Gln Asp Met Val Val Glu
            100                 105                 110

Gly Cys Gly Cys Arg
            115
```

(2) INFORMATION FOR SEQ ID NO:14:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: BMP-4

(ix) FEATURE:
        (A) NAME/KEY: Protein
        (B) LOCATION: 1..117

(xi) SEQUENCE DESCRIPTION: SEQ ID NO:14:

```
Arg Ser Pro Lys His His Ser Gln Arg Ala Arg Lys Lys Asn Lys Asn
1                   5                   10                  15

Cys Arg Arg His Ser Leu Tyr Val Asp Phe Ser Asp Val Gly Trp Asn
                20                  25                  30

Asp Trp Ile Val Ala Pro Pro Gly Tyr Gln Ala Phe Tyr Cys His Gly
            35                  40                  45

Asp Cys Pro Phe Pro Leu Ala Asp His Leu Asn Ser Thr Asn His Ala
    50                  55                  60

Ile Val Gln Thr Leu Val Asn Ser Val Asn Ser Ser Ile Pro Lys Ala
65                  70                  75                  80

Cys Cys Val Pro Thr Glu Leu Ser Ala Ile Ser Met Leu Tyr Leu Asp
                85                  90                  95

Glu Tyr Asp Lys Val Val Leu Lys Asn Tyr Gln Glu Met Val Val Glu
            100                 105                 110

Gly Cys Gly Cys Arg
            115
```

(2) INFORMATION FOR SEQ ID NO:15:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: DPP (ix) FEATURE:
        (A) NAME/KEY: Protein
        (B) LOCATION: 1..118

(xi) SEQUENCE DESCRIPTION: SEQ ID NO:15:

```
Lys Arg His Ala Arg Arg Pro Thr Arg Arg Lys Asn His Asp Asp Thr
1                   5                   10                  15
```

-continued

```
Cys Arg Arg His Ser Leu Tyr Val Asp Phe Ser Asp Val Gly Trp Asp
            20                  25                  30

Asp Trp Ile Val Ala Pro Leu Gly Tyr Asp Ala Tyr Tyr Cys His Gly
            35                  40                  45

Lys Cys Pro Phe Pro Leu Ala Asp His Phe Asn Ser Thr Asn His Ala
            50                  55                  60

Val Val Gln Thr Leu Val Asn Asn Met Asn Pro Gly Lys Val Pro Lys
65                  70                  75                  80

Ala Cys Cys Val Pro Thr Gln Leu Asp Ser Val Ala Met Leu Tyr Leu
                    85                  90                  95

Asn Asp Gln Ser Thr Val Val Leu Lys Asn Tyr Gln Glu Met Thr Val
            100                 105                 110

Val Gly Cys Gly Cys Arg
            115
```

(2) INFORMATION FOR SEQ ID NO:16:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: BMP-3

(ix) FEATURE:
        (A) NAME/KEY: Protein
        (B) LOCATION: 1..119

(xi) SEQUENCE DESCRIPTION: SEQ ID NO:16:

```
Gln Thr Leu Lys Lys Ala Arg Arg Lys Gln Trp Ile Glu Pro Arg Asn
1               5                   10                  15

Cys Ala Arg Arg Tyr Leu Lys Val Asp Phe Ala Asp Ile Gly Trp Ser
            20                  25                  30

Glu Trp Ile Ile Ser Pro Lys Ser Phe Asp Ala Tyr Tyr Cys Ser Gly
            35                  40                  45

Ala Cys Gln Phe Pro Met Pro Lys Ser Leu Lys Pro Ser Asn His Ala
            50                  55                  60

Thr Ile Gln Ser Ile Val Arg Ala Val Gly Val Val Pro Gly Ile Pro
65                  70                  75                  80

Glu Pro Cys Cys Val Pro Glu Lys Met Ser Ser Leu Ser Ile Leu Phe
                    85                  90                  95

Phe Asp Glu Asn Lys Asn Val Val Leu Lys Val Tyr Pro Asn Met Thr
            100                 105                 110

Val Glu Ser Cys Ala Cys Arg
            115
```

(2) INFORMATION FOR SEQ ID NO:17:

(i) SEQUENCE CHARACTERISTICS:
        (A) LENGTH: 115 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: MIS (ix) FEATURE:
        (A) NAME/KEY: Protein
        (B) LOCATION: 1..115

(xi) SEQUENCE DESCRIPTION: SEQ ID NO:17:

Pro Gly Arg Ala Gln Arg Ser Ala Gly Ala Thr Ala Ala Asp Gly Pro
1               5                   10                  15

Cys Ala Leu Arg Glu Leu Ser Val Asp Leu Arg Ala Glu Arg Ser Val
                20                  25                  30

Leu Ile Pro Glu Thr Tyr Gln Ala Asn Asn Cys Gln Gly Val Cys Gly
            35                  40                  45

Trp Pro Gln Ser Asp Arg Asn Pro Arg Tyr Gly Asn His Val Val Leu
        50                  55                  60

Leu Leu Lys Met Gln Ala Arg Gly Ala Ala Leu Ala Arg Pro Pro Cys
65                  70                  75                  80

Cys Val Pro Thr Ala Tyr Ala Gly Lys Leu Leu Ile Ser Leu Ser Glu
                85                  90                  95

Glu Arg Ile Ser Ala His His Val Pro Asn Met Val Ala Thr Glu Cys
                100                 105                 110

Gly Cys Arg
        115

(2) INFORMATION FOR SEQ ID NO:18:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: Inhibin alpha (ix) FEATURE:
        (A) NAME/KEY: Protein
        (B) LOCATION: 1..121

(xi) SEQUENCE DESCRIPTION: SEQ ID NO:18:

Leu Arg Leu Leu Gln Arg Pro Pro Glu Glu Pro Ala Ala His Ala Asn
1               5                   10                  15

Cys His Arg Val Ala Leu Asn Ile Ser Phe Gln Glu Leu Gly Trp Glu
                20                  25                  30

Arg Trp Ile Val Tyr Pro Pro Ser Phe Ile Phe His Tyr Cys His Gly
            35                  40                  45

Gly Cys Gly Leu His Ile Pro Pro Asn Leu Ser Leu Pro Val Pro Gly
        50                  55                  60

Ala Pro Pro Thr Pro Ala Gln Pro Tyr Ser Leu Leu Pro Gly Ala Gln
65                  70                  75                  80

Pro Cys Cys Ala Ala Leu Pro Gly Thr Met Arg Pro Leu His Val Arg
                85                  90                  95

Thr Thr Ser Asp Gly Gly Tyr Ser Phe Lys Tyr Glu Thr Val Pro Asn
                100                 105                 110

Leu Leu Thr Gln His Cys Ala Cys Ile
        115                 120

(2) INFORMATION FOR SEQ ID NO:19:

(i) SEQUENCE CHARACTERISTICS:
        (A) LENGTH: 121 amino acids (B) TYPE: amino acid
(C) STRANDEDNESS: single
(D) TOPOLOGY: linear (ii) MOLECULE TYPE: protein (vii) IMMEDIATE SOURCE:
   (B) CLONE: Inhibin betaA (ix) FEATURE:
   (A) NAME/KEY: Protein
   (B) LOCATION: 1..121

(xi) SEQUENCE DESCRIPTION: SEQ ID NO:19:

```
Arg Arg Arg Arg Arg Gly Leu Glu Cys Asp Gly Lys Val Asn Ile Cys
1               5                   10                  15

Cys Lys Lys Gln Phe Phe Val Ser Phe Lys Asp Ile Gly Trp Asn Asp
            20                  25                  30

Trp Ile Ile Ala Pro Ser Gly Tyr His Ala Asn Tyr Cys Glu Gly Glu
        35                  40                  45

Cys Pro Ser His Ile Ala Gly Thr Ser Gly Ser Ser Leu Ser Phe His
    50                  55                  60

Ser Thr Val Ile Asn His Tyr Arg Met Arg Gly His Ser Pro Phe Ala
65                  70                  75                  80

Asn Leu Lys Ser Cys Cys Val Pro Thr Lys Leu Arg Pro Met Ser Met
                85                  90                  95

Leu Tyr Tyr Asp Asp Gly Gln Asn Ile Ile Lys Lys Asp Ile Gln Asn
            100                 105                 110

Met Ile Val Glu Glu Cys Gly Cys Ser
        115                 120
```

(2) INFORMATION FOR SEQ ID NO:20:

(i) SEQUENCE CHARACTERISTICS:
      (A) LENGTH: 120 amino acids
      (B) TYPE: amino acid
      (C) STRANDEDNESS: single
      (D) TOPOLOGY: linear (ii) MOLECULE TYPE: protein (vii) IMMEDIATE SOURCE:
      (B) CLONE: Inhibin betaB (ix) FEATURE:
      (A) NAME/KEY: Protein
      (B) LOCATION: 1..120

(xi) SEQUENCE DESCRIPTION: SEQ ID NO:20:

```
Arg Ile Arg Lys Arg Gly Leu Glu Cys Asp Gly Arg Thr Asn Leu Cys
1               5                   10                  15

Cys Arg Gln Gln Phe Phe Ile Asp Phe Arg Leu Ile Gly Trp Asn Asp
            20                  25                  30

Trp Ile Ile Ala Pro Thr Gly Tyr Tyr Gly Asn Tyr Cys Glu Gly Ser
        35                  40                  45

Cys Pro Ala Tyr Leu Ala Gly Val Pro Gly Ser Ala Ser Ser Phe His
    50                  55                  60

Thr Ala Val Val Asn Gln Tyr Arg Met Arg Gly Leu Asn Pro Gly Thr
65                  70                  75                  80

Val Asn Ser Cys Cys Ile Pro Thr Lys Leu Ser Thr Met Ser Met Leu
                85                  90                  95

Tyr Phe Asp Asp Glu Tyr Asn Ile Val Lys Arg Asp Val Pro Asn Met
            100                 105                 110
```

```
Ile Val Glu Glu Cys Gly Cys Ala
        115                 120

(2) INFORMATION FOR SEQ ID NO:21:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: TGF-beta1

(ix) FEATURE:
        (A) NAME/KEY: Protein
        (B) LOCATION: 1..114

(xi) SEQUENCE DESCRIPTION: SEQ ID NO:21:

Arg Arg Ala Leu Asp Thr Asn Tyr Cys Phe Ser Ser Thr Glu Lys Asn
1               5                   10                  15

Cys Cys Val Arg Gln Leu Tyr Ile Asp Phe Arg Lys Asp Leu Gly Trp
            20                  25                  30

Lys Trp Ile His Glu Pro Lys Gly Tyr His Ala Asn Phe Cys Leu Gly
        35                  40                  45

Pro Cys Pro Tyr Ile Trp Ser Leu Asp Thr Gln Tyr Ser Lys Val Leu
    50                  55                  60

Ala Leu Tyr Asn Gln His Asn Pro Gly Ala Ser Ala Ala Pro Cys Cys
65              70                  75                  80

Val Pro Gln Ala Leu Glu Pro Leu Pro Ile Val Tyr Tyr Val Gly Arg
                85                  90                  95

Lys Pro Lys Val Glu Gln Leu Ser Asn Met Ile Val Arg Ser Cys Lys
            100                 105                 110

Cys Ser (2) INFORMATION FOR SEQ ID NO:22:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: TGF-beta2

(ix) FEATURE:
        (A) NAME/KEY: Protein
        (B) LOCATION: 1..114

(xi) SEQUENCE DESCRIPTION: SEQ ID NO:22:

Lys Arg Ala Leu Asp Ala Ala Tyr Cys Phe Arg Asn Val Gln Asp Asn
1               5                   10                  15

Cys Cys Leu Arg Pro Leu Tyr Ile Asp Phe Lys Arg Asp Leu Gly Trp
            20                  25                  30

Lys Trp Ile His Glu Pro Lys Gly Tyr Asn Ala Asn Phe Cys Ala Gly
        35                  40                  45

Ala Cys Pro Tyr Leu Trp Ser Ser Asp Thr Gln His Ser Arg Val Leu
    50                  55                  60
```

-continued

```
Ser Leu Tyr Asn Thr Ile Asn Pro Glu Ala Ser Ala Ser Pro Cys Cys
 65                  70                  75                  80

Val Ser Gln Asp Leu Glu Pro Leu Thr Ile Leu Tyr Tyr Ile Gly Lys
                 85                  90                  95

Thr Pro Lys Ile Glu Gln Leu Ser Asn Met Ile Val Lys Ser Cys Lys
                100                 105                 110

Cys Ser
```

(2) INFORMATION FOR SEQ ID NO:23:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: TGF-beta3

(ix) FEATURE:
        (A) NAME/KEY: Protein
        (B) LOCATION: 1..114

(xi) SEQUENCE DESCRIPTION: SEQ ID NO:23:

```
Lys Arg Ala Leu Asp Thr Asn Tyr Cys Phe Arg Asn Leu Glu Glu Asn
 1                   5                  10                  15

Cys Cys Val Arg Pro Leu Tyr Ile Asp Phe Arg Gln Asp Leu Gly Trp
                 20                  25                  30

Lys Trp Val His Glu Pro Lys Gly Tyr Tyr Ala Asn Phe Cys Ser Gly
             35                  40                  45

Pro Cys Pro Tyr Leu Arg Ser Ala Asp Thr Thr His Ser Thr Val Leu
 50                  55                  60

Gly Leu Tyr Asn Thr Leu Asn Pro Glu Ala Ser Ala Ser Pro Cys Cys
 65                  70                  75                  80

Val Pro Gln Asp Leu Glu Pro Leu Thr Ile Leu Tyr Tyr Val Gly Arg
                 85                  90                  95

Thr Pro Lys Val Glu Gln Leu Ser Asn Met Val Val Lys Ser Cys Lys
                100                 105                 110

Cys Ser
```

(2) INFORMATION FOR SEQ ID NO:24:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: TGF-beta4

(ix) FEATURE:
        (A) NAME/KEY: Protein
        (B) LOCATION: 1..116

(xi) SEQUENCE DESCRIPTION: SEQ ID NO:24:

```
Arg Arg Asp Leu Asp Thr Asp Tyr Cys Phe Gly Pro Gly Thr Asp Glu
 1                   5                  10                  15

Lys Asn Cys Cys Val Arg Pro Leu Tyr Ile Asp Phe Arg Lys Asp Leu
                 20                  25                  30
```

```
Gln Trp Lys Trp Ile His Glu Pro Lys Gly Tyr Met Ala Asn Phe Cys
            35                  40                  45

Met Gly Pro Cys Pro Tyr Ile Trp Ser Ala Asp Thr Gln Tyr Thr Lys
    50                  55                  60

Val Leu Ala Leu Tyr Asn Gln His Asn Pro Gly Ala Ser Ala Ala Pro
65                  70                  75                  80

Cys Cys Val Pro Gln Thr Leu Asp Pro Leu Pro Ile Ile Tyr Tyr Val
                85                  90                  95

Gly Arg Asn Val Arg Val Glu Gln Leu Ser Asn Met Val Val Arg Ala
            100                 105                 110

Cys Lys Cys Ser
        115

(2) INFORMATION FOR SEQ ID NO:25:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: TGF-beta5

(ix) FEATURE:
        (A) NAME/KEY: Protein
        (B) LOCATION: 1..114

(xi) SEQUENCE DESCRIPTION: SEQ ID NO:25:

Lys Arg Gly Val Gly Gln Glu Tyr Cys Phe Gly Asn Asn Gly Pro Asn
1               5                   10                  15

Cys Cys Val Lys Pro Leu Tyr Ile Asn Phe Arg Lys Asp Leu Gly Trp
            20                  25                  30

Lys Trp Ile His Glu Pro Lys Gly Tyr Glu Ala Asn Tyr Cys Leu Gly
            35                  40                  45

Asn Cys Pro Tyr Ile Trp Ser Met Asp Thr Gln Tyr Ser Lys Val Leu
    50                  55                  60

Ser Leu Tyr Asn Gln Asn Asn Pro Gly Ala Ser Ile Ser Pro Cys Cys
65                  70                  75                  80

Val Pro Asp Val Leu Glu Pro Leu Pro Ile Ile Tyr Tyr Val Gly Arg
                85                  90                  95

Thr Ala Lys Val Glu Gln Leu Ser Asn Met Val Val Arg Ser Cys Asn
            100                 105                 110

Cys Ser (2) INFORMATION FOR SEQ ID NO:26:

(i) SEQUENCE CHARACTERISTICS:
        (A) LENGTH: 454 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: HUMAN GDF-9

(ix) FEATURE:
        (A) NAME/KEY: Protein
        (B) LOCATION: 1..454
```

(xi) SEQUENCE DESCRIPTION: SEQ ID NO:26:

```
Met Ala Arg Pro Asn Lys Phe Leu Leu Trp Phe Cys Cys Phe Ala Trp
 1               5                  10                  15

Leu Cys Phe Pro Ile Ser Leu Gly Ser Gln Ala Ser Gly Gly Glu Ala
                20                  25                  30

Gln Ile Ala Ala Ser Ala Glu Leu Glu Ser Gly Ala Met Pro Trp Ser
            35                  40                  45

Leu Leu Gln His Ile Asp Glu Arg Asp Arg Ala Gly Leu Leu Pro Ala
50                  55                  60

Leu Phe Lys Val Leu Ser Val Gly Arg Gly Gly Ser Pro Arg Leu Gln
65                  70                  75                  80

Pro Asp Ser Arg Ala Leu His Tyr Met Lys Lys Leu Tyr Lys Thr Tyr
                85                  90                  95

Ala Thr Lys Glu Gly Ile Pro Lys Ser Asn Arg Ser His Leu Tyr Asn
            100                 105                 110

Thr Val Arg Leu Phe Thr Pro Cys Thr Arg His Lys Gln Ala Pro Gly
        115                 120                 125

Asp Gln Val Thr Gly Ile Leu Pro Ser Val Glu Leu Leu Phe Asn Leu
    130                 135                 140

Asp Arg Ile Thr Thr Val Glu His Leu Leu Lys Ser Val Leu Leu Tyr
145                 150                 155                 160

Asn Ile Asn Asn Ser Val Ser Phe Ser Ser Ala Val Lys Cys Val Cys
                165                 170                 175

Asn Leu Met Ile Lys Glu Pro Lys Ser Ser Arg Thr Leu Gly Arg
            180                 185                 190

Ala Pro Tyr Ser Phe Thr Phe Asn Ser Gln Phe Glu Phe Gly Lys Lys
        195                 200                 205

His Lys Trp Ile Gln Ile Asp Val Thr Ser Leu Leu Gln Pro Leu Val
    210                 215                 220

Ala Ser Asn Lys Arg Ser Ile His Met Ser Ile Asn Phe Thr Cys Met
225                 230                 235                 240

Lys Asp Gln Leu Glu His Pro Ser Ala Gln Asn Gly Leu Phe Asn Met
                245                 250                 255

Thr Leu Val Ser Pro Ser Leu Ile Leu Tyr Leu Asn Asp Thr Ser Ala
            260                 265                 270

Gln Ala Tyr His Ser Trp Tyr Ser Leu His Tyr Lys Arg Arg Pro Ser
        275                 280                 285

Gln Gly Pro Asp Gln Glu Arg Ser Leu Ser Ala Tyr Pro Val Gly Glu
    290                 295                 300

Glu Ala Ala Glu Asp Gly Arg Ser Ser His His Arg His Arg Arg Gly
305                 310                 315                 320

Gln Glu Thr Val Ser Ser Glu Leu Lys Lys Pro Leu Gly Pro Ala Ser
                325                 330                 335

Phe Asn Leu Ser Glu Tyr Phe Arg Gln Phe Leu Leu Pro Gln Asn Glu
            340                 345                 350

Cys Glu Leu His Asp Phe Arg Leu Ser Phe Ser Gln Leu Lys Trp Asp
        355                 360                 365

Asn Trp Ile Val Ala Pro His Arg Tyr Asn Pro Arg Tyr Cys Lys Gly
    370                 375                 380

Asp Cys Pro Arg Ala Val Gly His Arg Tyr Gly Ser Pro Val His Thr
385                 390                 395                 400

Met Val Gln Asn Ile Ile Tyr Glu Lys Leu Asp Ser Ser Val Pro Arg
```

-continued

```
                    405                 410                 415
Pro Ser Cys Val Pro Ala Lys Tyr Ser Pro Leu Ser Val Leu Thr Ile
            420                 425                 430

Glu Pro Asp Gly Ser Ile Ala Tyr Lys Glu Tyr Glu Asp Met Ile Ala
            435                 440                 445

Thr Lys Cys Thr Cys Arg
        450
```

GROWTH DIFFERENTIATION FACTOR-9 ANTIBODIES AND METHODS

This application is a divisional application of U.S. Ser. No. 08/491,835, filed Oct. 23, 1995, now U.S. Pat. No. 5,821,056, which is a continuation-in-part application of U.S. Ser. No. 08/003,303, filed Jan. 12, 1993, now abandoned.

BACKGROUND OF THE INVENTION

1. Field of the Invention

The invention relates generally to growth factors and specifically to a new member of the transforming growth factor beta (TGF-β) superfamily, which is denoted, growth differentiation factor-9 (GDF-9).

2. Description of Related Art

The transforming growth factor β (TGF-β) superfamily encompasses a group of structurally-related proteins which affect a wide range of differentiation processes during embryonic development. The family includes, Mullerian inhibiting substance (MIS), which is required for normal male sex development (Behringer, et al., *Nature*, 345:167, 1990), Drosophila decapentaplegic (DPP) gene product, which is required for dorsal-ventral axis formation and morphogenesis of the imaginal disks (Padgett, et al., *Nature*, 325:81–84, 1987). the Xenopus Vg-1 gene product, which localizes to the vegetal pole of eggs ((Weeks, et al., *Cell*, 51:861–867, 1987), the activins (Mason, et al., *Biochem, Biophys. Res. Commun.*, 135:957–964, 1986), which can induce the formation of mesoderm and anterior structures in Xenopus embryos (Thomsen, et al., *Cell*, 63:485, 1990), and the bone morphogenetic proteins (BMPs, osteogenin, OP-1) which can induce de novo cartilage and bone formation (Sampath, et al., *J. Biol. Chem.*, 265:13198, 1990). The TGF-βs can influence a variety of differentiation processes, including adipogenesis, myogenesis, chondrogenesis, hematopoiesis, and epithelial cell differentiation (for review, see Massague, *Cell* 49:437, 1987).

The proteins of the TGF-β family are initially synthesized as a large precursor protein which subsequently undergoes proteolytic cleavage at a cluster of basic residues approximately 110–140 amino acids from the C-terminus. The C-terminal regions of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. In each case, the active species appears to be a disulfide-linked dimer of C-terminal fragments. For most of the family members that have been studied, the homodimeric species has been found to be biologically active, but for other family members, like the inhibins (Ling, et al., *Nature*, 321:779, 1986) and the TGF-βs (Cheifetz, et al., *Cell*, 48:409, 1987), heterodimers have also been detected, and these appear to have different biological properties than the respective homodimers.

The inhibins and activins were originally purified from follicular fluid and shown to have counteracting effects on the release of follicle-stimulating hormone by the pituitary gland. Although the mRNAs for all three inhibin/activin subunits (αa, βA and βB) have been detected in the ovary, none of these appear to be ovary-specific (Meunier, et al., *Proc.Natl.Acad.Sci. USA*, 85:247, 1988). MIS has also been shown to be expressed by granulosa cells and the effects of MIS on ovarian development have been documented both in vivo in transgenic mice expressing MIS ectopically (Behringer, supra) and in vitro in organ culture (Vigier, et al., *Development*, 100:43, 1987).

Identification of new factors that are tissue-specific in their expression pattern will provide a greater understanding of that tissue's development and function.

SUMMARY OF THE INVENTION

The present invention provides a cell growth and differentiation factor, GDF-9, a polynucleotide sequence which encodes the factor and antibodies which are immunoreactive with the factor. This factor appears to relate to various cell proliferative disorders, especially those involving ovarian tumors, such as granulosa cell tumors.

Thus, in one embodiment, the invention provides a method for detecting a cell proliferative disorder of ovarian origin and which is associated with GDF-9. In another embodiment, the invention provides a method of treating a cell proliferative disorder associated with abnormal levels of expression of GDF-9, by suppressing or enhancing GDF-9 activity.

BRIEF DESCRIPTION OF THE DRAWINGS

FIGS. 2a–c shows nucleotide and predicted amino acid sequence of murine GDF-9 (SEQ ID NOS:3 and 4, respectively). Consensus N-glycosylation signals are denoted by plain boxes. The putative tetrabasic processing sites are denoted by stippled boxes. The in-frame termination codons upstream of the putative initiating ATG and the consensus polyadenylation signals are underlined. The poly A tails are not shown. Numbers indicate nucleotide position relative to the 5' end.

FIGS. 3a–b shows the alignment of the C-terminal sequences of GDF-9 with other members of the TGF-β family (SEQ ID NOS:5 to 25, respectively). The conserved cysteine residues are shaded. Dashes denote gaps introduced in order to maximize alignment.

FIGS. 4a–b shows amino acid homologies among the different members of the TGF-β superfamily. Numbers represent percent amino acid identities between each pair calculated from the first conserved cysteine to the C-terminus. Boxes represent homologies among highly-related members within particular subgroups.

FIG. 6 shows a comparison of the predicted amino acid sequences of murine (top lines SEQ ID No:4) and human (bottom lines SEQ ID NO:26) GDF-9. Numbers represent amino acid positions relative to the N-termini. Vertical lines represent sequence identities. Dots represent gaps introduced in order to maximize the alignment. The clear box shows the predicted proteolytic processing sites. The shaded boxes show the cysteine residues in the mature region of the proteins. The bars at the bottom show a schematic of the pre-(clear) and mature (shaded) regions of GDF-9 with the percent sequence identities between the murine and human sequences shown below.

FIGS. 7a–d shows in situ hybridization to adult ovary sections using a GDF-9 RNA probe. [$^{35}$S]-labeled anti-sense (FIGS. 7a and 7c) or sense (FIGS. 7b and 7d) GDF-9 RNA probes were hybridized to adjacent paraffin-embedded sections of ovaries fixed in 4% paraformaldehyde. Sections were dipped in photographic emulsion, exposed, developed, and then stained with hematoxylin and eosin. Two representative fields are shown.

DETAILED DESCRIPTION OF THE INVENTION

Figure 1:
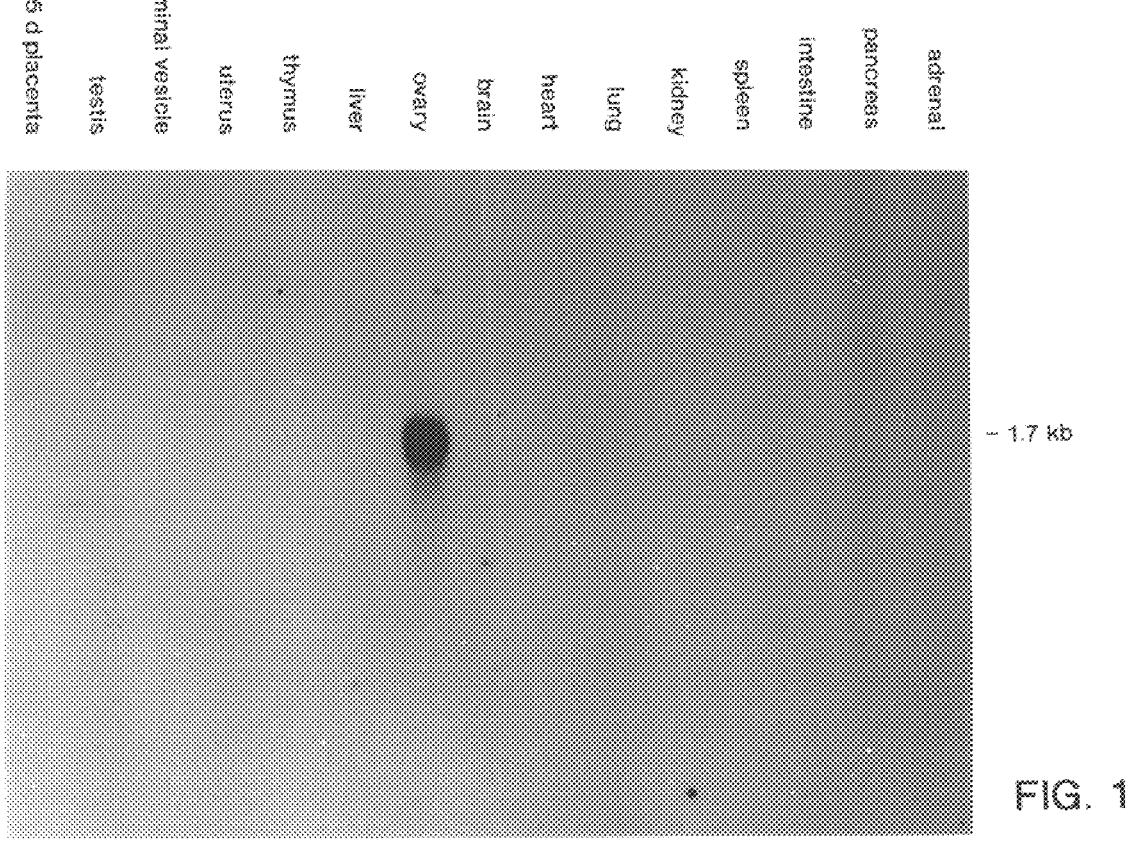
FIG. 1 shows expression of GDF-9 mRNA in adult tissues.

The present invention provides a growth and differentiation factor, GDF-9 and a polynucleotide sequence encoding GDF-9. Unlike other members of the TGF-β superfamily, GDF-9 expression is highly tissue specific, being expressed in cells primarily in ovarian tissue. In one embodiment, the invention provides a method for detection of a cell proliferative disorder of the ovary, which is associated with GDF-9 expression. In another embodiment, the invention provides a method for treating a cell proliferative disorder associated with abnormal expression of GDF-9 by using an agent which suppresses or enhances GDF-9 activity.

The TGF-β superfamily consists of multifunctionaly polypeptides that control proliferation, differentiation, and other functions in many cell types. Many of the peptides have regulatory, both positive and negative, effects on other peptide growth factors. The structural homology between the GDF-9 protein of this invention and the members of the TGF-β family, indicates that GDF-9 is a new member of the family of growth and differentiation factors. Based on the known activities of many of the other members, it can be expected that GDF-9 will also possess biological activities that will make it useful as a diagnostic and therapeutic reagent.

For example, another regulatory protein that has been found to have structural homology with TGF-β is inhibin, a specific and potent polypeptide inhibitor of the pituitary secretion of FSH. Inhibin has been isolated from ovarian follicular fluid. Because of its suppression of FSH, inhibin has potential to be used as a contraceptive in both males and females. GDF-9 may possess similar biological activity since it is also an ovarian specific peptide. Inhibin has also been shown to be useful as a marker for certain ovarian tumors (Lappohn, et al., N. Engl. J. Med., 321:790, 1989). GDF-9 may also be useful as a marker for identifying primary and metastatic neoplasms of ovarian origin. Similarly, GDF-9 may be useful as an indicator of developmental anomalies in prenatal screening procedures.

Another peptide of the TGF-β family is MIS, produced by the testis and responsible for the regression of the Mullerian ducts in the male embryo. MIS has been show to inhibit the growth of human ovarian cancer in nude mice (Donahoe, et al., Ann. Surg., 194:472, 1981). GDF-9 may function similarly and may, therefore, be useful as an anti-cancer agent, such as for the treatment of ovarian cancer.

GDF-9 may also function as a growth stimulatory factor and, therefore, be useful for the survival of various cell populations in vitro. In particular, if GDF-9 plays a role in oocyte maturation, it may be useful in in vitro fertilization procedures, e.g., in enhancing the success rate. Many of the members of the TGF-β family are also important mediators of tissue repair. TGF-β has been shown to have marked effects on the formation of collagen and causes a striking angiogenic response in the newborn mouse (Roberts, et al., Proc. Natl. Acad. Sci. USA, 83:4167, 1986). GDF-9 may also have similar activities and may be useful in repair of tissue injury caused by trauma or burns for example.

The term "substantially pure" as used herein refers to GDF-9 which is substantially free of other proteins, lipids, carbohydrates or other materials with which it is naturally associated. One skilled in the art can purify GDF-9 using standard techniques for protein purification. The substantially pure polypeptide will yield a single major band on a non-reducing polyacrylamide gel. The purity of the GDF-9 polypeptide can also be determined by amino-terminal amino acid sequence analysis. GDF-9 polypeptide includes functional fragments of the polypeptide, as long as the activity of GDF-9 remains. Smaller peptides containing the biological activity of GDF-9 are included in the invention.

The invention provides polynucleotides encoding the GDF-9 protein. These polynucleotides include DNA, cDNA and RNA sequences which encoae GDF-9. It is understood that all polynucleotides encoding all or a portion of GDF-9 are also included herein, as long as they encode a polypeptide with GDF-9 activity. Such polynucleotides include naturally occurring, synthetic, and intentionally manipulated polynucleotides. For example, GDF-9 polynucleotide may be subjected to site-directed mutagenesis. The polynucleotide sequence for GDF-9 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of GDF-9 polypeptide encoded by the nucleotide sequence is functionally unchanged.

Specifically disclosed herein is a cDNA sequence for GDF-9 which is 1712 base pairs in length and contains an open reading frame beginning with a methionine codon at nucleotide 29. The encoded polypeptide is 441 amino acids in length with a molecular weight of about 49.6 kD, as determined by nucleotide sequence analysis. The GDF-9 sequence contains a core of hydrophobic amino acids near the N-terminus, suggestive of a signal sequence for secretion. GDF-9 contains four potential N-glycosytation sites at asparagine residues 163, 229, 258, and 325 and a putative tetrabasic proteolytic processing site (RRRR) at amino acids 303–306. The mature C-terminal fragment of GDF-9 is predicted to be 135 amino acids in length and have an unglycosylated molecular weight of about 15.6 kD, as determined by nucleotide sequence analysis. One skilled in the art can modify, or partially or completely remove the glycosyl groups from the GDF-9 protein using standard techniques. Therefore, the functional protein or fragments thereof of the invention includes glycosylated, partially glycosylated and unglycosylated species of GDF-9.

The degree of sequence identity of GDF-9 with known TGF-β family members ranges from a minimum of 21% with Mullerian inhibiting substance (MIS) to a maximum of 34% with bone morphogenetic protein-4 (BMP-4). GDF-9 specifically disclosed herein differs from the known family members in its pattern of cysteine residues in the C-terminal region. GDF-9 lacks the fourth cysteine of the seven cysteines present in other family members; in place of cysteine at this position, the GDF-9 sequence contains a serine residue. This GDF-9 does not contain a seventh cysteine residue elsewhere in the C-terminal region.

Minor modifications of the recombinant GDF-9 primary amino acid sequence may result in proteins which have substantially equivalent activity as compared to the GDF-9 polypeptide described herein. Such modifications may be deliberate, as by site-directed mutagenesis, or may be spontaneous. All of the polypeptides produced by these modifications are included herein as long as the biological activity of GDF-9 still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which are not required for GDF-9 biological activity.

The nucleotide sequence encoding the GDF-9 polypeptide of the invention includes the disclosed sequence and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences and 2) antibody screening of expression libraries to detect cloned DNA fragments with shared structural features.

Preferably the GDF-9 polynucleotide of the invention is derived from a mammalian organism, and most preferably from a mouse, rat, or human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.,* 9:879, 1981).

The development of specific DNA sequences encoding GDF-9 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.,* 11:2325, 1983).

A cDNA expression library, such as lambda gt11, can be screened indirectly for GDF-9 peptides having at least one epitope, using antibodies specific for GDF-9. Such antibodies can be either polyclonally or monoclonally derived and used to detect expression product indicative of the presence of GDF-9 cDNA.

DNA sequences encoding GDF-9 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the GDF-9 polynucleotide sequences may be inserted into a recombinant expression vector. The term "recombinant expression vector" refers to a plasmid, virus or other vehicle known in the art that has been manipulated by insertion or incorporation of the GDF-9 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene*, 56:125, 1987), the pMSXND expression vector for expression in mammalian cells (Lee and Nathans, *J. Biol. Chem.*, 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding GDF-9 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the GDF-9 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The invention includes antibodies immunoreactive with GDF-9 polypeptide or functional fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., *Nature*, 256:495, 1975). The term antibody as used in this invention is meant to include intact molecules as well as fragments thereof, such as Fab and F(ab')$_2$, which are capable of binding an epitopic determinant on GDF-9.

The term "cell-proliferative disorder" denotes malignant as well as non-malignant cell populations which often appear to differ from the surrounding tissue both morphologically and genotypically. The GDF-9 polynucleotide that is an antisense molecule is useful in treating malignancies of the various organ systems, particularly, for example, the ovaries. Essentially, any disorder which is etiologically linked to altered expression of GDF-9 could be considered susceptible to treatment with a GDF-9 suppressing reagent.

The invention provides a method for detecting a cell proliferative disorder of the ovary which comprises contacting an anti-GDF-9 antibody with a cell suspected of having a GDF-9 associated disorder and detecting binding to the antibody. The antibody reactive with GDF-9 is labeled with a compound which allows detection of binding to GDF-9. For purposes of the invention, an antibody specific for GDF-9 polypeptide may be used to detect the level of GDF-9 in biological fluids and tissues. Any specimen containing a detectable amount of antigen can be used. A preferred sample of this invention is tissue of ovarian origin, specifically tissue containing granulosa cells or ovarian follicular fluid. The level of GDF-9 in the suspect cell can be compared with the level in a normal cell to determine whether the subject has a GDF-9-associated cell proliferative disorder. Preferably the subject is human.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The concentration of detectably labeled monoclonal antibody which is adminstered should be sufficient such that the binding to those cells having the polypeptide is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. Such dosages may vary, for example, depending on whether multiple injections are given, antigenic burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that deleterious radiation with respect to the host is minimized. Ideally, a radioisotope used for in vivo imaging will lack a particle emission, but produce a large number of photons in the 140–250 keV range, which may readily be detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used in vitro and in vivo to monitor the course of amelioration of a GDF-9-associated disease in a subject. Thus, for example, by measuring the increase or decrease in the number of cells expressing antigen comprising a polypeptide of the invention or changes in the concentration of such antigen present in various body fluids, it would be possible to determine whether a particular therapeutic regimen aimed at ameliorating the GDF-9-associated disease is effective. The term "ameliorate" denotes a lessening of the detrimental effect of the GDF-9-associated disease in the subject receiving therapy.

The present invention identifies a nucleotide sequence that can be expressed in an altered manner as compared to expression in a normal cell, therefore, it is possible to design appropriate therapeutic or diagnostic techniques directed to this sequence. Thus, where a cell-proliferative disorder is associated with the expression of GDF-9, nucleic acid sequences that interfere with GDF-9 expression at the translational level can be used. This approach utilizes, for example, antisense nucleic acid and ribozymes to block translation of a specific GDF-9 mRNA, either by masking that mRNA with an antisense nucleic acid or by cleaving it with a ribozyme.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target GDF-9-producing cell. The use of antisense methods to inhibit the in vitro translation of genes is well known in the art (Marcus-Sakura, *Anal.Biochem.*, 172:289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J.Amer.Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The present invention also provides gene therapy for the treatment of cell proliferative disorders which are mediated by GDF-9 protein. Such therapy would achieve its therapeutic effect by introduction of the GDF-9 antisense polynucleotide into cells having the proliferative disorder. Delivery of antisense GDF-9 polynucleotide can be achieved using a recombinant expression vector such as a chimeric virus or a colloidal dispersion system.

Especially preferred for therapeutic delivery of antisense sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a GDF-9 sequence of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the GDF-9 antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for GDF-9 antisense polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 µm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Due to the expression of GDF-9 in the reproductive tract, there are a variety of applications using the polypeptide, polynucleotide and antibodies of the invention, related to contraception, fertility and pregnancy. GDF-9 could play a role in regulation of the menstrual cycle and, therefore, could be useful in various contraceptive regimens.

The following examples are intended to illustrate but not limit the invention. While they are typical of those that might be used, other procedures known to those skilled in the art may alternatively be used.

EXAMPLE 1

Identification and Isolation of a Novel TGF-β Family Member

To identify a new member of the TGF-β superfamily, degenerate oligonucleotides were designed which corresponded to two conserved regions among the known family members: one region spanning the two tryptophan residues conserved in all family members except MIS and the other region spanning the invariant cysteine residues near the C-terminus. These primers were used for polymerase chain reactions on mouse genomic DNA followed by subcloning the PCR products using restriction sites placed at the 5' ends of the primers, picking individual E. coli colonies carrying these subcloned inserts, and using a combination of random sequencing and hybridization analysis to eliminate known members of the superfamily.

GDF-9 was identified from a mixture of PCR products obtained with the primers SJL160 (5'-CCGGAATTCGGITGG(G/C/A)A(G/A/T/C)(G/C/A)A(G/A/T/C) TGG(A/G)TI(A/G)TI(T/G)CICC-3') (SEQUENCE ID NO. 1) and SJL153 (5'-CCGGAATTC(A/G)CAI(G/C)C (A/G)CAIC(T/C)(G/A/T/C)(C/G/T)TIG(T/C)I(G/A)(T/C) CAT-3') (SEQUENCE ID NO. 2). PCR using these primers was carried out with 2 µg mouse genomic DNA at 94° C. for 1 min, 50° C. for 2 min, and 72° C. for 2 min for 40 cycles.

PCR products of approximately 280 bp were gel-purified, digested with Eco RI, gel-purified again, and subcloned in the Bluescript vector (Stratagene, San Diego. Calif.). Bacterial colonies carrying individual subclones were picked into 96 well microtiter plates, and multiple replicas were prepared by plating the cells onto nitrocellulose. The replicate filters were hybridized to probes representing known members of the family, and DNA was prepared from non-hybridizing colonies for sequence analysis.

The primer combination of SJL160 and SJL153, yielded three known sequences (inhibin $\beta$B, BMP-2, and BMP-4) and one novel sequence (designated GDF-9) among 145 subclones analyzed.

RNA isolation and Northern analysis were carried out as described previously (Lee,S. J., Mol. Endocrinol. 4:1034, 1990). An oligo dT-primed cDNA library was prepared from 2.5–3 µg of ovary poly A-selected RNA in the lambda ZAP II vector according to the instructions provided by Stratagene. The ovary library was not amplified prior to screening. Filters were hybridized as described previously (Lee, S.-J., Proc. Natl. Acad. Sci. USA., 88:4250–4254, 1991). DNA sequencing of both strands was carried out using the dideoxy chain termination method (Sanger, et al., Proc. Natl. Acad. Sci., USA, 74:5463–5467, 1977) and a combination of the S1 nuclease/exonuclease III strategy (Henikoff, S., Gene, 28:351–359, 1984) and synthetic oligonucleotide primers.

EXAMPLE 2

Expression Pattern and Sequence of GDF-9

To determine the expression pattern of GDF-9, RNA samples prepared from a variety of adult tissues were screened by Northern analysis. Five micrograms of twice polyA-selected RNA prepared from each tissue were electrophoresed on formaldehyde gels, blotted and probed with GDF-9. As shown in FIG. 1, the GDF-9 probe detected a 1.7 kb mRNA expressed exclusively in the ovary.

A mouse ovary cDNA library of $1.5 \times 10^6$ recombinant phage was constructed in lambda ZAP II and screened with a probe derived from the GDF-9 PCR product. The nucleotide sequence of the longest of nineteen hybridizing clones is shown in FIG. 2. Consensus N-glycosylation signals are denoted by plain boxes. The putative tetrabasic processing sites are denoted by stippled boxes. The in-frame termination codons upstream of the putative initiating ATG and the consensus polyadenylation signals are underlined. The poly A tails are not shown. Numbers indicate nucleotide position relative to the 5' end. The 1712 bp sequence contains a long open reading frame beginning with a methionine codon at nucleotide 29 and potentially encoding a protein 441 amino acids in length with a molecular weight of 49.6 kD. Like other TGF-$\beta$ family members, the GDF-9 sequence contains a core of hydrophobic amino acids near the N-terminus suggestive of a signal sequence for secretion. GDF-9 contains four potential N-glycosylation sites at asparagine residues 163. 229, 258, and 325 and a putative tetrabasic proteolytic processing site (RRRR) at amino acids 303–306. The mature C-terminal fragment of GDF-9 is predicted to be 135 amino acids in length and have an unglycosylated molecular weight of 15.6 kD.

Figure 3B:
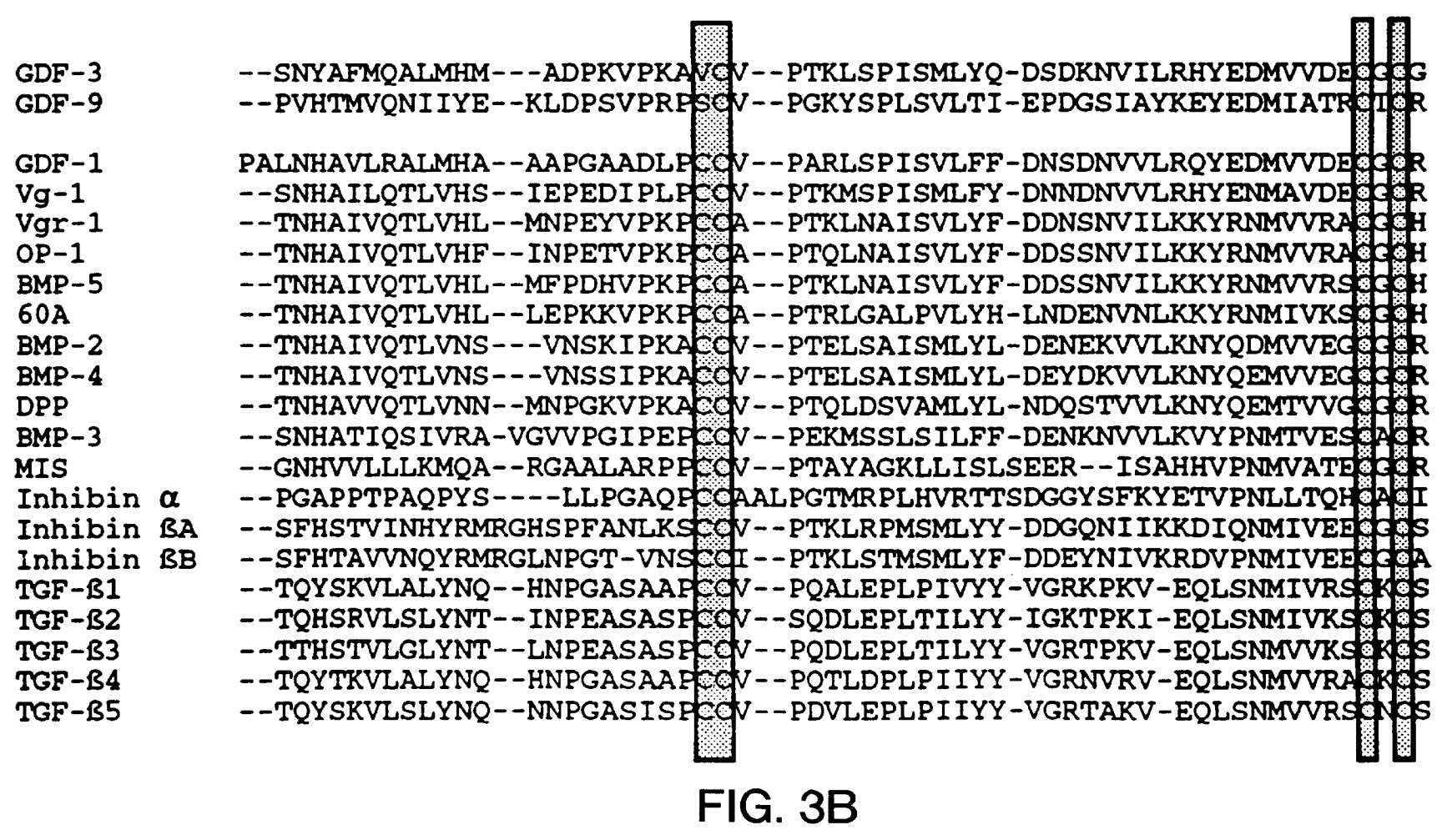

Although the C-terminal portion of GDF-9 clearly shows homology with the other family members, the sequence of GDF-9 is significantly diverged from those of the other family members (FIGS. 3 and 4). FIG. 3 shows the alignment of the C-terminal sequences of GDF-9 with the corresponding regions of human GDF-1 (Lee, Proc. Natl. Acad. Sci. USA, 88:4250–4254, 1991), Xenopus Vg-1 (Weeks, et al., Cell, 51:861–867, 1987), human Vgr-1 (Celeste, et al., Proc. Natl. Acad. Sci. USA, 87:9843–9847, 1990), human OP-1 (Ozkaynak, et al., EMBO J., 9:2085–2093, 1990), human BMP-5 (Celeste, et al., Proc. Natl. Acad. Sci. USA, 87:9843–9847, 1990), Drosophila 60A (Wharton, et al., Proc. Natl. Acad. Sci. USA, 88:9214–9218, 1991), human BMP-2 and 4 (Wozney, et al., Science, 242:1528–1534, 1988), Drosophila DPP (Padgett, et al., Nature, 325:81–84, 1987), human BMP-3 (Wozney, et al., Science, 242:1528–1534, 1988), human MIS (Cate, et al., Cell, 45:685–698, 1986), human inhibin, $\beta$A, and $\beta$B (Mason, et al., Biochem, Biophys. Res. Commun., 135:957–964, 1986), human TGF-$\beta$1 (Derynck, et al., Nature, 316:701–705, 1985), humanTGF-$\beta$2 (deMartin, et al., EMBO J., 6:3673–3677, 1987), human TGF-$\beta$3 (ten Dijke, et al., Proc. Natl. Acad. Sci. USA, 85:4715–4719, 1988), chicken TGF-$\beta$4 (Jakowlew, et al., Mol. Endocrinol., 2:1186–1195, 1988), and Xenopus TGF-$\beta$5 (Kondaiah, et al., J. Biol. Chem., 265:1089–1093, 1990). The conserved cysteine residues are shaded. Dashes denote gaps introduced in order to maximize the alignment.

FIG. 4 shows the amino acid homologies among the different members of the TGF-$\beta$ superfamily. Numbers represent percent amino acid identities between each pair calculated from the first conserved cysteine to the C-terminus. Boxes represent homologies among highly-related members within particular subgroups.

The degree of sequence identify with known family members ranges from a minimum of 21% with MIS to a maximum of 34% with BMP-4. Hence, GDF-9 is comparable to MIS in its degree of sequence divergence from the other members of this superfamily. Moreover, GDF-9 shows no significant sequence homology to other family members in the pro-region of the molecule. GDF-9 also differs from the known family members in its pattern of cysteine residues in the C-terminal region. GDF-9 lacks the fourth cysteine of the seven cysteines that are present in all other family members; in place of cysteine at this position, the GDF-9 sequence contains a serine residue. In addition, GDF-9 does not contain a seventh cysteine residue elsewhere in the C-terminal region.

EXAMPLE 3

Immunochemical Localization of GDF-9 in the Zona Pellucida

To determine whether GDF-9 mRNA was translated, sections of adult ovaries were incubated with antibodies directed against recombinant GDF-9 protein. In order to raise antibodies against GDF-9, portions of GDF-9 cDNA spanning amino acids 30 to 295 (pro-region) or 308 to 441

(mature region) were cloned into the T7-based pET3 expression vector (provided by F. W. Studier, Brookhaven National Laboratory), and the resulting plasmids were transformed into the BL21 (DE3) bacterial strain. Total cell extracts from isopropyl β-D-thiogalactoside-induced cells were electrophoresed on SDS/polyacrylamide gels, and the GDF-9 protein fragments were excised, mixed with Freund's adjuvant, and used to immunize rabbits by standard methods known to those of skill in the art. All immunizations were carried out by Spring Valley Lab (Sykesville, Md.). The presence of GDF-9-reactive antibodies in the sera of these rabbits was assessed by Western analysis of bacterially-expressed protein fragments. The resulting serum was shown to react with the bacterially-expressed protein by Western analysis.

Figure 5A:
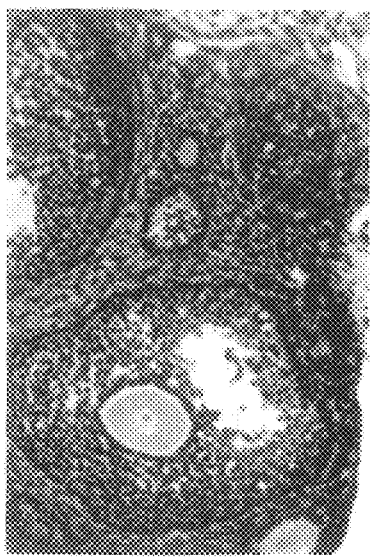
FIGS. 5a–c shows the immunohistochemical localization of GDF-9 protein. Adjacent sections of an adult ovary were either stained with hematoxylin and eosin (FIG. 5a) or incubated with immune (FIG. 5b) or pre-immune (FIG. 5c) serum at a dilution of 1:500. Anti-GDF-9 antiserum was prepared by expressing the C-terminal portion of murine GDF-9 (residues 308–441) in bacteria, excising GDF-9 protein from preparative SDS gels, and immunizing rabbits. Sites of antibody binding were visualized using the Vectastain ABC kit (Vector Labs).
Figure 5B:
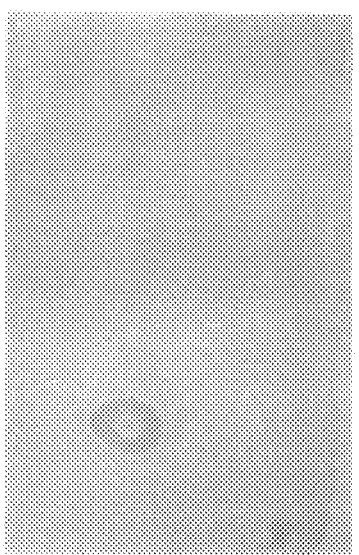
Figure 5C:
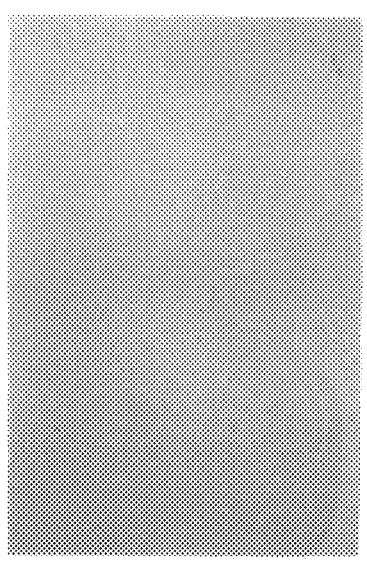

For immunohistochemical studies, ovaries were removed from adult mice, fixed in 4% paraformaldehyde, embedded in paraffin, and sectioned. Sites of antibody binding were detected by using the Vectastain ABC kit, according to the instructions provided by Vector Laboratories. FIG. 5 shows the immunohistochemical localization of GDF-9 protein. Adjacent sections of an adult ovary were either stained with hematoxylin and eosin (FIG. 5a) or incubated with immune (FIG. 5b) or pre-immune (FIG. 5c) serum at a dilution of 1:500. As shown in FIG. 5b, the antiserum detected protein solely in oocytes. No staining was detected using pre-immune serum (FIG. 5c). Hence, GDF-9 protein appears to translated in vivo by oocytes.

EXAMPLE 4

Isolation of Human GDF-9

In order to isolate a cDNA clone encoding human GDF-9, a cDNA library was constructed in lambda ZAP II using poly A-selected RNA prepared from an adult human ovary. From this library, a cDNA clone containing the entire human GDF-9 coding sequence was identified using standard screening techniques as in Example 1 and using the murine GDF-9 clone as a probe. A comparison of the predicted amino acid sequences of murine (top lines) and human (bottom lines) GDF-9 is shown in FIG. 6. Numbers represent amino acid positions relative to the N-termini. Vertical lines represent sequence identities. Dots represent gaps introduced in order to maximize the alignment. The clear box shows the predicted proteolytic processing sites. The shaded boxes show the cysteine residues in the mature region of the proteins. The bars at the bottom show a schematic of the pre-(clear) and mature (shaded) regions of GDF-9 with the percent sequence identities between the murine and human sequences shown below.

Like murine GDF-9, human GDF-9 contains a hydrophobic leader sequence, a putative RXXR proteolytic cleavage site, and a C-terminal region containing the hallmarks of other TGF-β family members. Murine and human GDF-9 are 64% identical in the pro- region and 90% identical in the predicted mature region of the molecule. The high degree of homology between the two sequences suggests that human GDF-9 plays an important role during embryonic development and/or in the adult ovary.

EXAMPLE 5

Nucleic Acid Detection of Expression of GDF-9 in Oocytes

In order to localize the expression of GDF-9 in the ovary, in situ hybridization to mouse ovary sections was carried out using an antisense GDF-9 RNA probe. FIG. 7 shows in situ hybridization to adult ovary sections using a GDF-9 RNA probe. [$^{35}$S]-labeled anti-sense (FIGS. 7a and 7c) or sense (FIGS. 7b and 7d) GDF-9 RNA probes were hybridized to adjacent paraffin-embedded sections of ovaries fixed in 4% paraformaldehyde. Sections were dipped in photographic emulsion, exposed, developed, and then stained with hematoxylin and eosin. Two representative fields are shown.

As shown in FIGS. 7a and 7c, GDF-9 mRNA was detected primarily in oocytes in adult ovaries. Every oocyte (regardless of the stage of follicular development) examined showed GDF-9 expression, and no expression was detected in any other cell types. No hybridization was seen using a control GDF-9 sense RNA probe (FIGS. 7b and 7d). Hence, GDF-9 expression appears to be oocyte-specific in adult ovaries.

Figure 8A:
FIGS. 8a–b shows in situ hybridization to a postnatal day 4 ovary section using an antisense GDF-9 RNA probe. Sections were prepared as described for FIG. 7. Following autoradiography and staining, the section was photographed under bright-field (FIG. 8a) or dark-field (FIG. 8b) illumination.
Figure 8B:
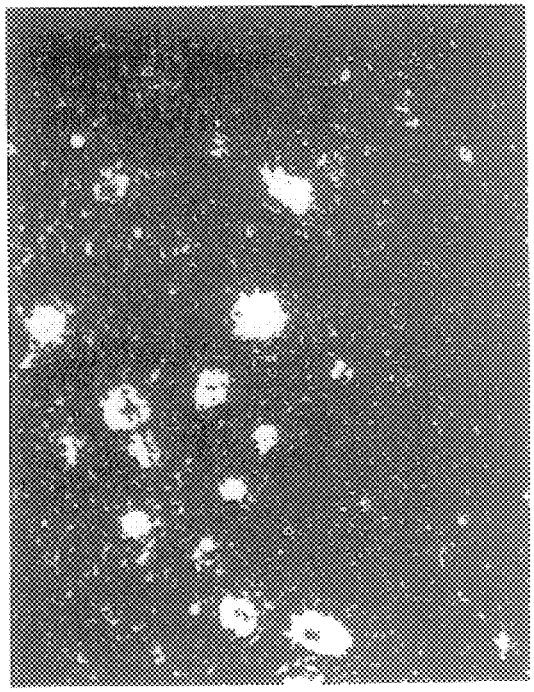

To determine the pattern of expression of GDF-9 mRNA during ovarian development, sections of neonatal ovaries were probed with a GDF-9 RNA probe. FIG. 8 shows in situ hybridization to a postnatal day 4 ovary section using an antisense GDF-9 RNA probe. Sections were prepared as described for FIG. 7. Following autoradiography and staining, the section was photographed under bright-field (FIG. 8a) or dark-field (FIG. 8b) illumination.

Figure 9A:
FIGS. 9a–b shows in situ hybridization to postnatal day 8 ovary sections using an antisense (FIG. 9a) or sense (FIG. 9b) GDF-9 RNA probe. Sections were prepared as described for FIG. 7.
Figure 9B:

FIG. 9 shows in situ hybridization to postnatal day 8 ovary sections using an antisense (FIG. 9a) or sense (FIG. 9b) GDF-9 RNA probe. Sections were prepared as described for FIG. 7. GDF-9 mRNA expression was first detected at the onset of follicular development. This was most clearly evident at postnatal day 4, where only oocytes that were present in follicles showed GDF-9 expression (FIG. 8); no expression was seen in oocytes that were not surrounded by granulosa cells. By postnatal day 8, every oocyte appeared to have undergone follicular development, and every oocyte showed GDF-9 expression (FIG. 9).

Figure 10A:
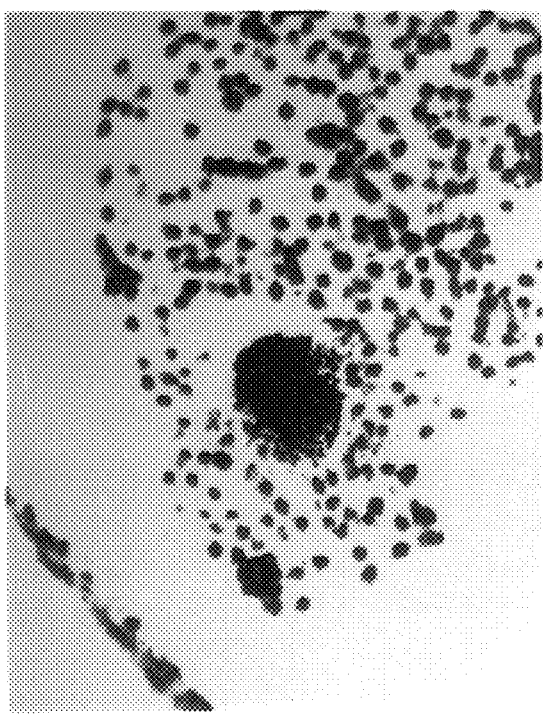
FIG. 10 shows in situ hybridization to adult oviduct sections using an antisense (FIG. 10a) or sense (FIG. 10b) GDF-9 RNA probe. Sections were prepared as described for FIG. 7.
Figure 10B:

To determine whether GDF-9 was also expressed following ovulation, sections of mouse oviducts were examined by in situ hybridization. FIG. 10 shows in situ hybridization to adult oviduct sections using an antisense (FIG. 10a) or sense (FIG. 10b) GDF-9 RNA probe. Sections were prepared as described for FIG. 7.

Figure 11A:
FIGS. 11a–b shows in situ hybridization to an adult oviduct (0.5 days following fertilization) section using an antisense GDF-9 RNA probe. Sections were prepared as described for FIG. 7. Following autoradiography and staining, the section was photographed under bright-field (FIG. 11a) or dark-field (FIG. 11b) illumination.
Figure 11B:
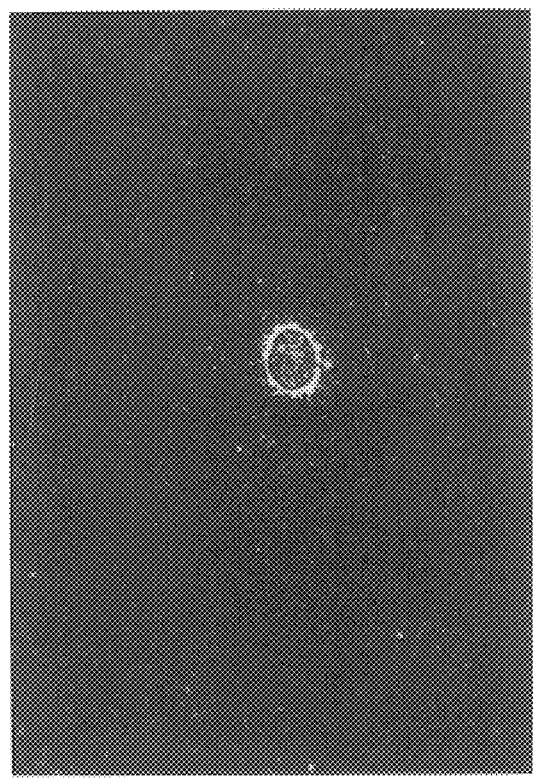

FIG. 11 shows in situ hybridization to an adult oviduct (0.5 days following fertilization) section using an antisense GDF-9 RNA probe. Sections were prepared as described for FIG. 7. Following autoradiography and staining, the section was photographed under bright-field (FIG. 11a) or dark-field (FIG. 11b) illumination.

As shown in FIG. 10, GDF-9 was expressed by oocytes that had been released into the oviduct. However, the expression of GDF-9 mRNA turned off rapidly following fertilization of the oocytes; by day 0.5 following fertilization, only some embryos (such as the one shown in FIG. 11) expressed GDF-9 mRNA, and by day 1.5, all embryos were negative for GDF-9 expression.

Although the invention has been described with reference to the presently preferred embodiment, it should be understood that various modifications can be made without departing from the spirit of the invention. Accordingly, the invention is limited only by the following claims.

SUMMARY OF SEQUENCES

Sequence ID No. 1 is the nucleotide sequence for the primer, SJL160, for GDF-9 (page 24, lines 15 and 16);

Sequence ID No. 2 is the nucleotide sequence for the primer, SJL153, for GDF-9 (page 24, lines 17 and 18);

Sequence ID No. 3 is the nucleotide and deduced amino acid sequence for GDF-9 (FIG. 2);

Sequence ID No. 4 is the deduced amino acid sequence for GDF-9 (FIG. 2);
Sequence ID No. 5 is the amino acid sequence of the C-terminus of GDF-3 (FIG. 3);
Sequence ID No. 6 is the amino acid sequence of the C-terminus of GDF-9 (FIG. 3);
Sequence ID No. 7 is the amino acid sequence of the C-terminus of GDF-1 (FIG. 3);
Sequence ID No. 8 is the amino acid sequence of the C-terminus of Vg-1 (FIG. 3);
Sequence ID No. 9 is the amino acid sequence of the C-terminus of Vgr-1 (FIG. 3);
Sequence ID No. 10 is the amino acid sequence of the C-terminus of OP-1 (FIG. 3);
Sequence ID No. 11 is the amino acid sequence of the C-terminus of BMP-5 (FIG. 3);
Sequence ID No. 12 is the amino acid sequence of the C-terminus of 60A (FIG. 3);
Sequence ID No. 13 is the amino acid sequence of the C-terminus of BMP-2 (FIG. 3);
Sequence ID No. 14 is the amino acid sequence of the C-terminus of BMP-4 (FIG. 3);
Sequence ID No. 15 is the amino acid sequence of the C-terminus of DPP (FIG. 3);
Sequence ID No. 16 is the amino acid sequence of the C-terminus of BMP-3 (FIG. 3);
Sequence ID No. 17 is the amino acid sequence of the C-terminus of MIS (FIG. 3);
Sequence ID No. 18 is the amino acid sequence of the C-terminus of inhibin α (FIG. 3);
Sequence ID No. 19 is the amino acid sequence of the C-terminus of inhibin βA (FIG. 3);
Sequence ID No. 20 is the amino acid sequence of the C-terminus of inhibin βB (FIG. 3);
Sequence ID No. 21 is the amino acid sequence of the C-terminus of TGF-β1 (FIG. 3);
Sequence ID No. 22 is the amino acid sequence of the C-terminus of TGF-β2 (FIG. 3);
Sequence ID No. 23 is the amino acid sequence of the C-terminus of TGF-β3 (FIG. 3);
Sequence ID No. 24 is the amino acid sequence of the C-terminus of TGF-β4 (FIG. 3);
Sequence ID No. 25 is the amino acid sequence of the C-terminus of TGF-β5 (FIG. 3); and
Sequence ID No. 26 is the amino acid sequence of human GDF-9 (FIG. 6).

What is claimed is:

1. An antibody that specifically binds to a growth differentiation factor-9 (GDF-9) polypeptide of SEQ ID NOS: 4 or 26, or binds to antigenic fragments thereof.

2. The antibody of claim 1, wherein the antibody is polyclonal.

3. The antibody of claim 1, wherein the antibody is monoclonal.

4. A method of detecting or quantifying the levels of a GDF-9 polypeptide having the sequence of SEQ ID NOs: 4 or 26 in a sample comprising contacting a sample with an antibody that specifically binds to growth differentiation factor-9 (GDF-9) polypeptide of SEQ ID NOS: 4 or 26, or binds to antigenic fragments thereof and detecting binding of the antibody.

5. The method of claim 4, wherein the sample is tissue from a tumor.

6. The method of claim 4, wherein the detecting is in vivo.

7. The method of claim 4, wherein the antibody is labeled with a detectable label.

8. The method of claim 7, wherein the detectable label is selected from the group consisting of a radioisotope, a fluorescent compound, a bioluminescent compound and a chemiluminescent compound.

9. The method of claim 4, wherein the detection is in vitro.

* * * * *